United States Patent
Dhawan et al.

(10) Patent No.: US 12,312,291 B2
(45) Date of Patent: May 27, 2025

(54) OXYGENATED AROMATIC AMINES AND USE AS ANTIOXIDANTS

(71) Applicant: Ecolab USA Inc., St. Paul, MN (US)

(72) Inventors: Ashish Dhawan, Aurora, IL (US); Abuzar Syed, Richmond, TX (US); Janelle Pennington, Missouri City, TX (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 16/860,922

(22) Filed: Apr. 28, 2020

(65) Prior Publication Data

US 2020/0339503 A1   Oct. 29, 2020

Related U.S. Application Data

(60) Provisional application No. 62/840,133, filed on Apr. 29, 2019.

(51) Int. Cl.
| | |
|---|---|
| *C07C 217/76* | (2006.01) |
| *C07C 213/08* | (2006.01) |
| *C10L 1/223* | (2006.01) |

(52) U.S. Cl.
CPC .......... *C07C 217/76* (2013.01); *C07C 213/08* (2013.01); *C10L 1/2235* (2013.01); *C10L 2230/081* (2013.01)

(58) Field of Classification Search
CPC . C07C 217/76; C10L 1/2235; C10L 2230/081
See application file for complete search history.

(56) References Cited

U.S. PATENT DOCUMENTS

| | | | | |
|---|---|---|---|---|
| 2,518,577 A | * | 8/1950 | Chenicek | C11B 5/0035 554/7 |
| 2,797,152 A | * | 6/1957 | Hughes | C10L 1/2235 44/428 |
| 2,861,998 A | | 11/1958 | Reynolds et al. | |
| 2,864,797 A | | 12/1958 | De Groote et al. | |
| 2,907,801 A | | 10/1959 | Johnson et al. | |

(Continued)

FOREIGN PATENT DOCUMENTS

| | | |
|---|---|---|
| CA | 467388 A | 8/1950 |
| DE | 343151 C | 10/1921 |

(Continued)

OTHER PUBLICATIONS

Kluchesky et al. (1949) "Polymerization Inhibition and Stopping Agents", Ind. Eng. Chem., 41:1768-1771.

(Continued)

*Primary Examiner* — Ellen M McAvoy
*Assistant Examiner* — Ming Cheung Po
(74) *Attorney, Agent, or Firm* — Kagan Binder, PLLC

(57) ABSTRACT

Described are compounds, compositions, and methods that include oxygenated aromatic amines, such as an aminophenol-, phenyl-p-phenylenediamine-, and diaminobenzene-based compound useful as antioxidants. The oxygenated aromatic amine includes a secondary and/or tertiary amine group having a nitrogen that is attached to one or two carbon-containing group(s), the carbon-containing group(s) having a hydroxyl and/or ether group separated from the nitrogen by one or more carbon atoms.

22 Claims, 4 Drawing Sheets

(56) References Cited

U.S. PATENT DOCUMENTS

| | | | |
|---|---|---|---|
| 3,010,912 A | 11/1961 | Hardman | |
| 3,432,401 A | 3/1969 | Tcherkawsky et al. | |
| 3,678,113 A * | 7/1972 | Klopfer | C10L 1/222 |
| | | | 564/409 |
| 3,696,050 A | 10/1972 | Werts, III et al. | |
| 3,697,275 A | 10/1972 | Hayakawa et al. | |
| 3,959,358 A | 5/1976 | Jursich | |
| 3,992,307 A * | 11/1976 | Hotten | C10M 141/10 |
| | | | 508/495 |
| 4,003,800 A | 1/1977 | Bacha et al. | |
| 4,021,310 A | 5/1977 | Shimizu et al. | |
| 4,038,434 A * | 7/1977 | Young | A23L 3/3526 |
| | | | 554/7 |
| 4,117,238 A | 9/1978 | Ackermann et al. | |
| 4,337,103 A | 6/1982 | Elrick et al. | |
| 4,374,742 A | 2/1983 | Evans et al. | |
| 4,585,796 A | 4/1986 | Alig et al. | |
| 4,654,451 A | 3/1987 | Miller et al. | |
| 4,675,444 A | 6/1987 | Matsunaga et al. | |
| 4,692,544 A | 9/1987 | Goerner et al. | |
| 4,744,881 A | 5/1988 | Reid | |
| 5,103,032 A | 4/1992 | Turner et al. | |
| 5,213,699 A * | 5/1993 | Babiarz | C07C 211/55 |
| | | | 508/513 |
| 5,219,480 A | 6/1993 | Gutierrez et al. | |
| 5,266,442 A | 11/1993 | Ooms | |
| 5,320,765 A | 6/1994 | Fetterman, Jr. et al. | |
| 5,340,369 A | 8/1994 | Koch et al. | |
| 5,443,596 A | 8/1995 | Junino et al. | |
| 5,476,973 A | 12/1995 | Hatano et al. | |
| 5,583,247 A | 12/1996 | Nesvadba et al. | |
| 5,728,872 A | 3/1998 | Riemenschneider | |
| 5,763,144 A | 6/1998 | Jeganathan | |
| 5,909,337 A | 6/1999 | Tyndall, III | |
| 6,024,769 A | 2/2000 | Cotteret | |
| 6,040,482 A | 3/2000 | Harris et al. | |
| 6,200,461 B1 | 3/2001 | Eldin | |
| 6,452,020 B1 | 9/2002 | Batlaw et al. | |
| 6,639,026 B2 | 10/2003 | Eldin | |
| 7,045,647 B2 | 5/2006 | Benage | |
| 7,204,858 B2 | 4/2007 | Desenne et al. | |
| 7,498,467 B2 | 3/2009 | Shiraki | |
| 7,569,615 B2 | 8/2009 | Leinweber et al. | |
| 7,671,098 B2 | 3/2010 | Leinweber et al. | |
| 7,900,590 B2 | 3/2011 | Cleveland et al. | |
| 7,902,317 B2 | 3/2011 | Kumar et al. | |
| 8,530,397 B2 * | 9/2013 | Bera | C10M 135/26 |
| | | | 508/545 |
| 9,168,217 B2 | 10/2015 | Schweinsberg | |
| 9,212,330 B2 | 12/2015 | Bolton et al. | |
| 9,266,797 B2 | 2/2016 | Colorado, Jr. et al. | |
| 10,308,886 B2 * | 6/2019 | Rana | C10G 29/26 |
| 2001/0050700 A1 | 12/2001 | Smith et al. | |
| 2002/0156136 A1 * | 10/2002 | Holtrup | C08G 8/36 |
| | | | 516/184 |
| 2003/0065177 A1 | 4/2003 | Sheridan et al. | |
| 2003/0111331 A1 | 6/2003 | Chalfant et al. | |
| 2003/0217418 A1 | 11/2003 | Fadel et al. | |
| 2004/0211702 A1 | 10/2004 | Link et al. | |
| 2005/0209117 A1 | 9/2005 | Friedrich et al. | |
| 2008/0045666 A1 | 2/2008 | Snell et al. | |
| 2008/0090742 A1 | 4/2008 | Mathur | |
| 2012/0056128 A1 | 3/2012 | Thoret Bauchet | |
| 2013/0186629 A1 | 7/2013 | Leonard et al. | |
| 2014/0259884 A1 | 9/2014 | Sunkara et al. | |
| 2019/0117541 A1 | 4/2019 | Consoli et al. | |
| 2020/0172831 A1 | 6/2020 | Dhawan et al. | |
| 2020/0339503 A1 | 10/2020 | Dhawan et al. | |
| 2020/0339880 A1 | 10/2020 | Masere et al. | |

FOREIGN PATENT DOCUMENTS

| | | |
|---|---|---|
| EP | 0145588 | 6/1985 |
| EP | 0449546 A1 | 10/1991 |
| GB | 748856 | 5/1956 |
| GB | 2030581 A | 4/1980 |
| GB | 1567047 | 5/1980 |
| JP | 6340570 | 12/1994 |
| JP | 2011256314 A | 12/2011 |
| JP | 2014017050 A | 1/2014 |
| RU | 2046804 C1 | 10/1995 |
| WO | 2005037206 A2 | 4/2005 |
| WO | 2020113218 A2 | 6/2020 |

OTHER PUBLICATIONS

Voronkov et al. (1978) "XRN=2846043" Journal of General Chemistry of the USSR, vol. 48, 2 pages, abstract.

Ladona et al. (1999) "Biotransformation and Clearance of 3-(Phenylamino)propane-1,2-diol, a Compound Present in Samples Related to Toxic Oil Syndrome, in C57BL/6 and A/J Mice", Chem. Res. Toxicol., 12:1127-1137.

Zeinalova et al. (1977) "Inhibition of the oxidation of synthetic oils at high temperatures", Chemistry and Technology of Fuels and Oils, 13:40-42.

Habib et al. (2012) "Synthesis of Some Novel Antioxidantand Anticorrosive Additives for Egyptian Lubricating Oils" Petroleum Science and Technology, 30:2435-2449.

Ionova et al. (2011) "Synthesis, Structure, and Properties of New Antioxidants Basedon Hydroxpropylated p-Aminodiphenylamine", Petroleum Chemistry, 51(6):454-457.

Arnold, J.S., et al. (2012) "Rhodium-Catalyzed Dynamic Kinetic Asymmetric Transformations of Racemic Tertiary Allylic Trichloroacetimidates with Anilines", Journal of American Chemical Society, 134:8380-8383.

* cited by examiner

OXYGENATED AROMATIC AMINES AND USE AS ANTIOXIDANTS

CROSS REFERENCE TO RELATED APPLICATION

This application claims the benefit of U.S. Provisional Patent Application Ser. No. 62/840,133 filed Apr. 29, 2019, the disclosure of which is incorporated by reference herein in its entirety.

TECHNICAL FIELD

The invention is directed to compositions and use of oxygenated aromatic amines as antioxidants

BACKGROUND

Antioxidants are used in various types of compositions and industries. For example, antioxidants are used to inhibit chemical oxidation of compositions obtained in the petroleum and gas industries. Antioxidants also play important roles as food preservatives, and are often added to various food compositions to preserve food properties.

Hydrocarbon-containing compositions can benefit from use of antioxidants. In fats and oils, antioxidants can inhibit oxidation reactions which can otherwise undesirably affect the chemistries of such fats and oils. In food products, the oxidation of edible fats and oils can lead to unpleasant odors and tastes, causing spoilage of the food. Oxidation can be caused by exposure to oxygen and sunlight that lead to oxidation of hydrocarbons.

Antioxidants are also added to fuels, such as gasoline and gasoline/ethanol blends, and lubricants to prevent oxidation of hydrocarbons therein. Gasoline fuels can oxidize easily upon exposure to conditions such as heat, oxygen, and ultraviolet light. Oxidation products result in gum or sediment within the fuel and thereby leading to problems such as plugging and corrosion of internal combustion engines. Antioxidants can prevent the polymerization of compounds in gasoline otherwise leading to residues that can damage internal combustion engines.

Plastic, rubber, and adhesive compositions can also benefit from the addition of antioxidants to prevent oxidative damage of polymers otherwise resulting in loss of flexibility and strength of the composition. Oxidative damage to polymer compositions often results in cracks in the material surface that is exposed to oxygen and/or UV radiation.

Some convention antioxidants need to be used at elevated concentrations to provide antioxidant activity, poorly control peroxides that are formed during oxidation, and are poorly effective at stopping color degradation of fuels. As such, there is a need for a gasoline or gasoline and ethanol blend composition having improved oxidation stability that reduces or eliminates sedimentation and gum formation within the fuel and concomitantly, reduces or eliminates corrosion or plugging of internal combustion engines.

SUMMARY

The current disclosure is directed toward oxygenated aromatic amines compounds, such as aminophenol-, n-phenyl-p-phenylenediamine-, and diaminobenzene-based compounds, as well as compositions and methods that include or utilize the compounds for preventing oxidation of organic compounds (i.e., as antioxidants).

The invention provides compounds of Formula I which are used in methods of the disclosure, the compound of Formula I being:

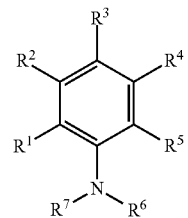

wherein $-R^1$, $-R^2$, $-R^3$, $-R^4$, and $-R^5$ are independently selected from $-H$, $-OH$, alkyl, aryl, alkyl aryl and aryl alkyl, and $-NR^8R^9$, wherein $R^8$ and $R^9$ are independently selected from $-H$, alkyl, aryl, alkyl aryl and aryl alkyl, and $R^6/R^7$ as described herein, or any two adjacent groups of $-R^1$, $-R^2$, $-R^3$, $-R^4$, and $-R^5$ form one or more ring structures. One or both of $R^6$ and $R^7$ is/are (i) a carbon-containing group including one or more hydroxyl group(s) separated from the N atom by one or more carbon atoms; if $R^6$ or $R^7$ is not (i) then it is selected from $-H$, alkyl, aryl, alkyl aryl and aryl alkyl.

In embodiments, at least one of $-R^1$, $-R^2$, $-R^3$, $-R^4$, and $-R^5$ is $-OH$, and preferably $-R^3$ is $-OH$. In some embodiments, those $-R^1$, $-R^2$, $-R^3$, $-R^4$, and $-R^5$ that are not $-OH$ are $-H$, and include aminophenols of the disclosure.

Other compounds of Formula I include those wherein one or more of $-R^1$, $-R^2$, $-R^3$, $-R^4$, and $-R^5$ is/are $-NR^8R^9$, and those $-R^1$, $-R^2$, $-R^3$, $-R^4$, and $-R^5$ that are not $-NR^8R^9$ are $-H$, and include diaminobenzene compounds of the disclosure.

In some embodiments, one or both of $R^6$ and $R^7$ are of the formula: $-(CR^{10}_2)_q(CHOH)(CH_2)_zR^{11}$, $R^{10}$ is independently selected from $-H$ and alkyl, wherein q and z are independently $(-)$ (a covalent bond), or an integer in the range of 1-12, preferably $(-)$, 1, or 2, and $R^{11}$ is selected from the group consisting of C1-C24 linear, branched, or cyclic alkyl, aryl, alkyl-aryl, and aryl-alkyl. Exemplary compounds include 4-bis[(hydroxyalkyl)amino]phenols and 1,4-bis[hydroxy-alkylamino]benzenes.

In other embodiments, one or both of $R^6$ and $R^7$ are of the formula: $-(CR^{10}_2)_q(CHOH)(R^{12}O)_zR^{11}$, $R^{10}$ is independently selected from $-H$ and alkyl, wherein q is $(-)$ (a covalent bond) or an integer in the range of 1-12, preferably $(-)$, 1, or 2, and $R^{11}$ is selected from the group consisting of C1-C24 linear, branched, or cyclic alkyl, aryl, alkyl-aryl, and aryl-alkyl, and $R^{12}$ is independently selected from $-(CH_2)_w-$, wherein w is 1, 2, or 3. Exemplary compounds include 4-bis[(alkoxy-hydroxy-alkyl)amino]phenols and 1,4-bis[alkoxy-hydroxy-alkylamino]benzenes.

In embodiments, the invention provides a method for inhibiting oxidation of an organic compound, the method comprising: adding a compound of Formula I to a composition comprising an organic compound, wherein the compound of Formula I inhibits oxidation of the organic compound in the composition. The compound protected against oxidation can be one present in a fuel composition, a lubricant composition, a rubber composition, a plastic composition, or an adhesive composition.

The invention also provides a method for preparing a compound of Formula I. In the method, an aryl-group containing reactant having either (a) a primary amine and a hydroxyl group; (b) two primary amine groups; (c) a primary and a secondary amine group, or (d) a primary and a tertiary amine group, is reacted with a carbon and oxygen-containing reactant, capable of reaction with the primary amine group, and/or optionally secondary amine group to provide a compound of Formula I, as described herein.

Exemplary reactants include those aryl group reactants that are 4-aminophenol, 1,4-diaminobenzene (p-phenylenediamine), and dimethyl-4-phenylenediamine, and oxirane- and oxitane-containing reactants, such as those according to Formula II:

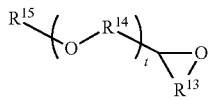

wherein $R^{13}$ is —$(CH_2)$— or —$(CH_2CH_2)$—, wherein $R^{14}$ is —$(CH_2)_w$—, wherein w is an integer in the range of 1-3, t is an integer in the range of 1-100, and wherein $R^{15}$ is $R^{10}$, as described herein, optionally substituted with one or more hydroxyl groups The oxygenated aromatic amines compounds described herein display significantly better antioxidant performance than other known antioxidants, and protect against oxidative, thermal degradation of organic materials. These antioxidants generally have comparatively higher antioxidant properties along with improved thermal stability and performance in a wide range of materials including but not limited to petroleum-based products (lubricants, gasoline, aviation fuels, and engine oils), plastics, elastomers, cosmetics, cooking oil, and food products.

In turn, acting as antioxidants, the oxygenated aromatic amines can inhibit fouling in a composition that includes an organic compound. The antioxidant can accordingly hinder the formation of polymers, prepolymers, oligomers and/or other materials which would otherwise become insoluble in and/or precipitate from a stream and deposit on articles that are in contact with the treated composition.

Further, methods of preparing the oxygenated aromatic amines compounds described herein allow for improved synthesis and quality of compositions including these antioxidants. For example, the disclosed processes can be efficiently and economically performed in the melt phase and therefore do not require, or minimize the use of extraneous materials, such as catalysts and solvents. Further, the methods for preparing the oxygenated aromatic amines compounds can generally reduce or eliminate purification steps for the final product compared to existing syntheses. In turn, this can lead to a superior performance/cost ratio for the product and a reduced amount of waste.

DETAILED DESCRIPTION

Figure 1:
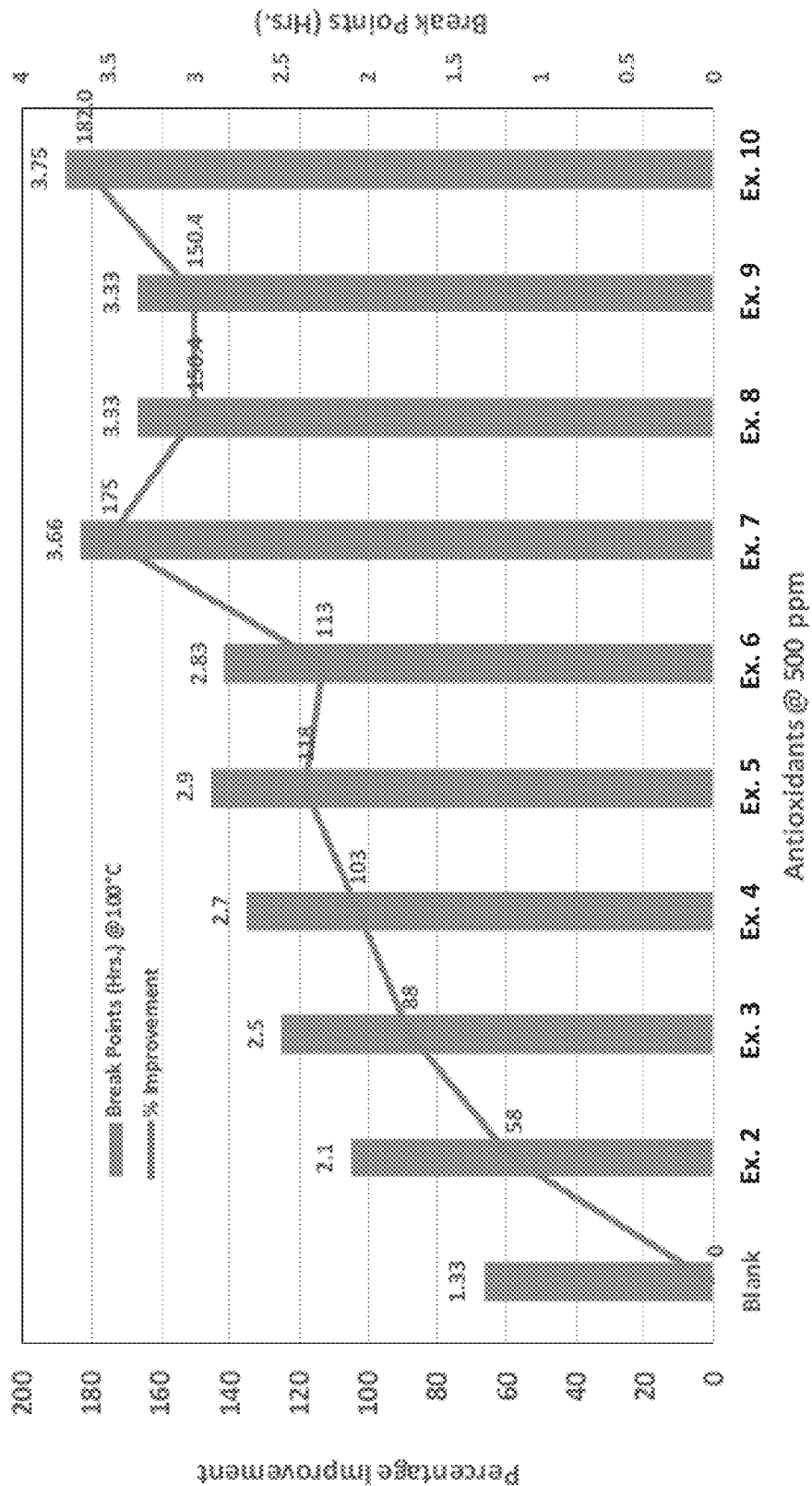
FIG. 1 is a graph of the duration (hours) until reaching pressure break points as determined from antioxidant testing of various oxygenated aromatic amines of the disclosure with heavy coker naphtha.

Although the present disclosure provides references to preferred embodiments, persons skilled in the art will recognize that changes may be made in form and detail without departing from the spirit and scope of the invention. Reference to various embodiments does not limit the scope of the claims attached hereto. Additionally, any examples set forth in this specification are not intended to be limiting and merely set forth some of the many possible embodiments for the appended claims.

Additional advantages and novel features of the invention will be set forth in part in the description that follows, and in part will become apparent to those skilled in the art upon examination of the following, or may be learned through routine experimentation upon practice of the invention.

Compositions and methods of the disclosure include or use compounds having a nitrogen- and oxygen-containing aromatic chemistry (oxygenated aromatic amines). The oxygenated aromatic amines include, in the least, an unsaturated 6 carbon ring structure having at least one nitrogen atom of a secondary or tertiary amine group bonded to an aromatic ring carbon, with the nitrogen atom of the secondary or tertiary amine group attached to a first carbon-containing group (and optionally a second carbon-containing group), that includes one or more hydroxyl group(s) and/or ether group(s) separated from the N atom by one or more carbon atoms. Preferably, the first carbon-containing group (and optionally a second carbon-containing group), includes one or more hydroxyl group(s) and one or more ether group(s) separated from the N atom by one or more carbon atoms. Preferably, hydroxyl group and ether group are separated from the nitrogen by two carbon atoms, or by three carbon atoms. The oxygenated aromatic amines also includes at least either a hydroxyl group, or a second amine group (which can be the same or different than the aforementioned secondary or tertiary amine group) bonded to another aromatic ring carbon. Atoms on the aromatic ring that are not bonded to the secondary or tertiary amine group, and the hydroxyl or second amine group, can be bonded to a hydrogen atom, a hydrocarbon group including an aryl and/or alkyl group, or can form a ring structure (e.g., forming a fused ring structure with the aromatic ring)

In some embodiments, the oxygenated aromatic amines has an unsaturated 6 carbon ring structure and bonded to a ring atom(s) one or more hydroxyl groups in addition to the secondary or tertiary amine group. The unsaturated 6 carbon ring structure can be an aryl ring or can be part of a fused ring structure that includes an unsaturated 6 carbon ring structure. Exemplary compounds of the disclosure that include a hydroxyl group bonded to a ring atom of an unsaturated 6 carbon ring include those based on phenol, pyrocatechol, resorcinol, hydroquinone, hydroxyl-hydroquinone, or phlorolucitol. Exemplary compounds also include those based on hydroxyl-containing fused aromatic chemistries such as naphthol, hydroxyl-anthracene, or indenol.

In some embodiments, the oxygenated aromatic amines has an unsaturated 6 carbon ring structure has bonded to a ring atom(s) one or more amine groups in addition to the secondary or tertiary amine group that includes at least the first carbon-containing group. The unsaturated 6 carbon ring structure can be an aryl ring or can be part of a fused ring structure that includes an unsaturated 6 carbon ring structure. Exemplary compounds of the disclosure that include an amine group bonded to a ring atom of an unsaturated 6 carbon ring include those based on aniline, benzenediamine, and benzenetriamine. Exemplary compounds also include those based on hydroxyl-containing fused aromatic chemistries such as naphthylamine, diaminonaphthalene, aminoanthracene, indenylamine, and indenyldiamine.

In embodiments, the first and/or second carbon-containing group(s) of the secondary or tertiary amine group include: a number of carbon atoms in the range of 1 to about 24, 2 to about 23, or 2 to about 22; a number of hydrogen atoms in the range of 3 to about 40, 4 to about 38, or 5 to about 35; a number of oxygen atoms of 1, 2, 3, or 4; or any combination thereof. In preferred embodiments, the carbon containing groups of the secondary or tertiary amine group include only carbon, oxygen, and hydrogen.

In some embodiments, the current disclosure provides "bis" compounds wherein the compound includes a tertiary amine group, and the first carbon-containing group and the second carbon-containing group bonded to the nitrogen atom of the tertiary amine group are the same. For example, in the aminophenol compound 4-bis[(3-butoxy-2-hydroxypropyl)amino]phenol, the first and second carbon-containing groups are the same and are —(CH$_2$CHOHCH$_2$)O(CH$_2$)$_3$CH$_3$.

Other "bis" compounds include those based on diamines, such as phenylenediamines, where the compounds include a first secondary amine group bonded to a ring carbon, and a second secondary amine group bonded to a ring carbon, wherein the first and second amine group are further bonded to carbon-containing groups that include a hydroxyl group, an ether group, or both, wherein the carbon-containing groups are the same. For example, in the diaminobenzene compound 1,4-bis[3-hexyloxy-2-hydroxy-propylamino] benzene the first and second carbon-containing groups are the same and are —(CH$_2$CHOHCH$_2$)O(CH$_2$)$_5$CH$_3$.

Compounds of the disclosure are described with reference to Formula I:

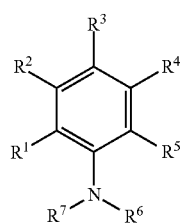

(I)

In Formula I —$R^1$, —$R^2$, —$R^3$, —$R^4$, and —$R^5$ are independently selected from —H, —OH, alkyl, aryl, alkyl aryl and aryl alkyl, and —NR$^8$R$^9$. $R^8$ and $R^9$ are independently selected from —H, alkyl, aryl, alkyl aryl and aryl alkyl and $R^6$/$R^7$ as described herein, or any two adjacent groups of —$R^1$, —$R^2$, —$R^3$, —$R^4$, and —$R^5$ form one or more ring structures. One or both of $R^6$ and $R^7$ is or are (i) a carbon-containing group that includes one or more hydroxyl group(s) and/or ether groups separated from the N atom by one or more carbon atoms, If $R^6$ or $R^7$ is not (i) then it is selected from —H, alkyl, aryl, alkyl aryl and aryl alkyl.

Exemplary alkyl groups that can be one or more of —$R^1$, —$R^2$, —$R^3$, —$R^4$, —$R^5$, —$R^8$, and —$R^9$ can be alkyl groups having a number of carbon atoms in the range of 1-18, 1-12, 1-8, 1-6, or 1-3, and selected from linear, branched, and cyclic alkyl groups. Exemplary alkyl group species include, but are not limited to:
methyl,
ethyl,
propyl, isopropyl,
butyl, isobutyl, sec-butyl, tert-butyl,
pentyl, cyclopentyl, isopentyl, neopentyl,
hexyl, cyclohexyl, 1-, 2-, and 3-methylbutyl, 1,1-, 1,2-, or 2,2-dimethylpropyl, 1-ethyl-propyl, 1-, 2-, 3-, or 4-methylpentyl, 1,1-, 1,2-, 1,3-, 2,2-, 2.3-, or 3,3-dimethylbutyl, 1- or 2-ethylbutyl, 1-ethyl-1-methylpropyl, and 1,1,2- or 1,2,2-trimethylpropyl, methylcyclopentyl;
heptyl, 2-methylhexyl, 3-methylhexyl, 4-methylhexyl, 5-methylhexyl, 3-ethylpentyl, 2,2,3-trimethylbutyl, 2,2-dimethylpentyl, 2,3-dimethylpentyl, 2,4-dimethylpentyl, 3,3-dimethylpentyl, 3,4-dimethylpentyl, 4,4-dimethylpentyl, cycloheptyl, 1-methylcyclohexyl, and 2-methylcyclohexyl;
octyl, 2-methylheptyl 3-methylheptyl, 4-methylheptyl, 2-ethylhexyl, 3-ethylhexyl, 4-ethylhexyl, 5-ethylhexyl, 2,2-dimethylhexyl, 2,3-dimethylhexyl, 2,4-dimethylhexyl, 2,5-dimethylhexyl, 3,3-dimethylhexyl, 3,4-dimethylhexyl, 3-ethyl-2-methylpentyl, 3-ethyl-3-methylpentyl, 2,2,3-trimethylpentyl, 2,2,4-trimethylpentyl, 2,3,3-trimethylpentyl, 2,3,4-trimethylpentyl, and 2,2,3,3-tetramethylbutyl;
nonyl, decyl, undecyl, dodecyl, tridecyl, tetradecyl, pentadecyl, hexadecyl, heptadecyl, and octadecyloxy.

Exemplary alkyl aryl groups that can be one or more of —$R^1$, —$R^2$, —$R^3$, —$R^4$, —$R^5$, —$R^8$, and —$R^9$ can be alkyl aryl groups having a number of carbon atoms in the range of 7-18 or 7-12, such as phenmethyl, phenethyl, phenpropyl, phenisopropyl, phenbutyl, penisobutyl, phen-sec-butylene, phen-tert-butylene, phen-pentylene, and hexylene, etc.

Exemplary aryl alkyl groups that can be one or more of —$R^1$, —$R^2$, —$R^3$, —$R^4$, —$R^5$, —$R^8$, and —$R^9$ can be aryl alkyl groups having a number of carbon atoms in the range of 7-18 or 7-12, such as methyl-phenyl, ethyl-phenyl, propyl-phenyl, butyl-phenyl, pentyl-phenyl, hexyl-phenyl, heptyl-phenyl, and octyl-phenyl.

In embodiments, in one or both of $R^6$ and $R^7$, one or more hydroxyl group(s) and/or ether group(s) are separated from the N atom by two or more carbon atoms, and preferably by two carbon atoms.

In embodiments, one or both of $R^6$ and $R^7$ include one or more oxygen atoms in the form of one or more hydroxyl groups. In some embodiments, one or both of $R^6$ and $R^7$ are of the formula: —(CR$^{10}$$_2$)$_q$(CHOH)(CH$_2$)$_z$R$^{11}$, where $R^{10}$ is independently selected from —H and alkyl, wherein q and z are independently (—) (a covalent bond), or an integer in the range of 1-12, and $R^{11}$ is selected from the group consisting of C1-C24 linear, branched, or cyclic alkyl, aryl, alkyl-aryl, and aryl-alkyl. Preferably q and z are independently (—), 1, or 2. Even more preferably $R^{10}$ is —H; q is 1; z is (—); and $R^{11}$ is selected from C1-C18 linear, branched, or cyclic alkyl, aryl, alkyl-aryl, and aryl-alkyl groups. Exemplary alkyl, alkyl-aryl, and aryl-alkyl groups are described herein. Exemplary species of the formula: —(CR$^{10}$$_2$)$_q$(CHOH)(CH$_2$)$_z$R$^{11}$, include the following groups:

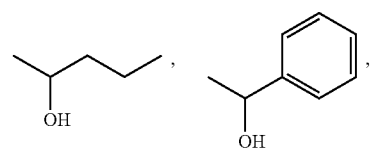

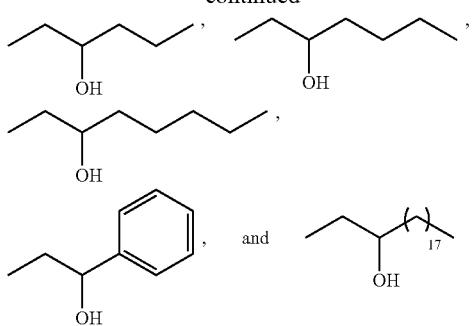

, and 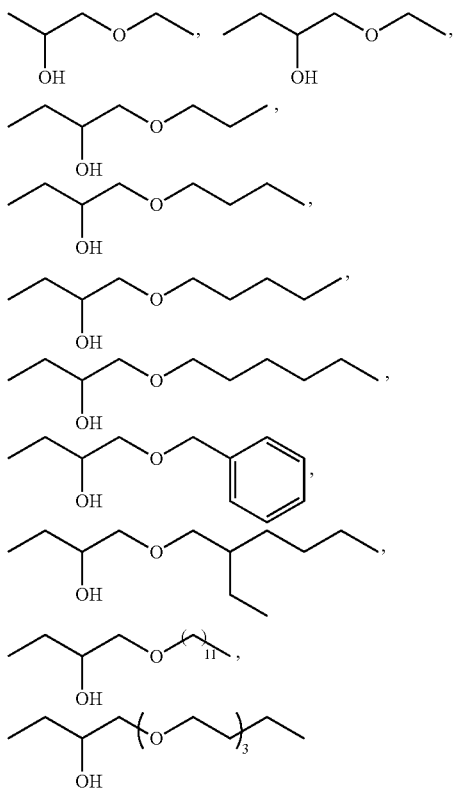

In embodiments, one or both of $R^6$ and $R^7$ include two or more oxygen atoms at least one in the form a hydroxyl group(s) and at least one in the form of an ether group(s). In some embodiments, one or both of $R^6$ and $R^7$ are of the formula: $-(CR^{10}_2)_q(CHOH)(R^{12}O)_zR^{11}$, where $R^{10}$ is independently selected from $-H$ and alkyl, wherein q is (—) (a covalent bond) or an integer in the range of 1-12, and $R^{11}$ is selected from C1-C24 linear, branched, or cyclic alkyl, aryl, alkyl-aryl, and aryl-alkyl groups, and $R^{12}$ is independently selected from $-(CH_2)_w-$, wherein w is 1, 2, or 3, and wherein z is an integer in the range of 1-100, 1-50, 1-25, 1-15, 1-10, 1-5, or t is 2, 3, or 4. In preferred aspects, $R^{10}$ is —H; q is 1; z is 1; w is 1 or 2, and $R^1$ is C1-C18 linear, branched, or cyclic alkyl, aryl, alkyl-aryl, and aryl-alkyl. Exemplary alkyl, alkyl-aryl, and aryl-alkyl groups are described herein.

Exemplary species of the formula: $(CR^{10}_2)_q(CHOH)(R^{12}O)_zR^{11}$, include the following groups:

Preferred compounds of Formula I include those wherein one or more of $-R^1$, $-R^2$, $-R^3$, $-R^4$, and $-R^5$ is —OH, and those $-R^1$, $-R^2$, $-R^3$, $-R^4$, and $-R^5$ that are not —OH are —H. For example, some preferred compounds of the disclosure have the following sub-Formula Ia, wherein $R^6$ and $R^7$ have the meanings described herein.

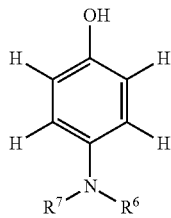

Ia

Exemplary compounds of sub-Formula Ia include, wherein both of $R^6$ and $R^7$ are of the formula: $-(CR^{10}_2)_q(CHOH)(CH_2)_zR^{11}$, 4-bis[(2-hydroxyethyl)amino]phenol, 4-bis[(2-hydroxypropyl)amino]phenol, 4-bis[(2-hydroxybutyl)amino]phenol, 4-bis[(2-hydroxypentyl)amino]phenol, 4-bis[(2-hydroxyhexyl)amino]phenol, 4-bis[(2-hydroxy-2-phenyl)amino]phenol, 4-bis[(2-hydroxy-2-phenylethyl)amino]phenol, 4-bis[(2-hydroxyheptyl)amino]phenol, 4-bis[(2-hydroxyoctyl)amino]phenol, 4-bis[(2-hydroxynonyl)amino]phenol, 4-bis[(2-hydroxydecyl)amino]phenol, 4-bis[(2-hydroxyundecyl)amino]phenol, 4-bis[(2-hydroxydodecyl)amino]phenol, 4-bis[(2-hydroxytridecyl)amino]phenol, 4-bis[(2-hydroxytetradecyl)amino]phenol, 4-bis[(2-hydroxypentadecyl)amino]phenol, 4-bis[(2-hydroxyhexadecyl)amino]phenol, 4-bis[(2-hydroxyheptadecyl)amino]phenol, 4-bis[(2-hydroxyoctadecyl)amino]phenol, 4-bis[(2-hydroxyeleyl)amino]phenol, 4-bis[(2-hydroxynonadecyl)amino]phenol, 4-bis[(2-hydroxyeicosyl)amino]phenol, 4-bis[(2-hydroxyheneicosyl)amino]phenol, 4-bis[(2-hydroxydocosyl)amino]phenol, and 4-bis[(2-hydroxytricosyl)amino]phenol.

Other exemplary compounds of sub-Formula Ia wherein both of $R^6$ and $R^7$ are of the formula: $-(CR^{10}_2)_q(CHOH)(R^{12}O)_zR^{11}$ include, but are not limited to, 4-bis[(3-methoxy-2-hydroxy-propyl)amino]phenol, 4-bis[(3-ethoxy-2-hydroxy-propyl)amino]phenol, 4-bis[(3-propoxy-2-hydroxy-propyl)amino]phenol, 4-bis[(3-butoxy-2-hydroxy-propyl)amino]phenol, 4-bis[(3-pentyloxy-2-hydroxy-propyl)amino]phenol, 4-bis[(3-hexyloxy-2-hydroxy-propyl)amino]phenol, 4-bis[(3-heptyloxy-2-hydroxy-propyl)amino]phenol, 4-bis[(3-octyloxy-2-hydroxy-propyl)amino]phenol, 4-bis[(3-nonyloxy-2-hydroxy-propyl)amino]phenol, 4-bis[(3-decyloxy-2-hydroxy-propyl)amino]phenol, 4-bis[(3-undecyloxy-2-hydroxy-propyl)amino]phenol, 4-bis[(3-dodecyloxy-2-hydroxy-propyl)amino]phenol, 4-bis[(3-tridecyloxy-2-hydroxy-propyl)amino]phenol, 4-bis[(3-tetradecyloxy-2-hydroxy-propyl)amino]phenol, 4-bis[(3-pentadecyloxy-2-hydroxy-propyl)amino]phenol, 4-bis[(3-hexadecyloxy-2-hydroxy-propyl)amino]phenol, 4-bis[(3-heptadecyloxy-2-hydroxy-propyl)amino]phenol, 4-bis[(3-octadecyloxy-2-hydroxy-propyl)amino]phenol, 4-bis[(3-eleyloxy-2-hydroxy-propyl)amino]phenol, 4-bis[(3-nonadecyloxy-2-hydroxy-propyl)amino]phenol, 4-bis[(3-eicosyloxy-2-hydroxy-propyl)amino]phenol, 4-bis[(3-heneicosyloxy-2-hydroxy-propyl)amino]phenol, 4-bis[(3-docosyloxy-2-hydroxy-propyl)amino]phenol, and 4-bis[(3-tricosyloxy-2-hydroxy-propyl)amino]phenol.

Other preferred compounds of Formula I include those wherein one or more of $-R^1$, $-R^2$, $-R^3$, $-R^4$, and $-R^5$ is/are $-NR^8R^9$, with $R^8$ and $R^9$ independently selected from —H, alkyl, aryl, alkyl aryl and aryl alkyl and $R^6/R^7$ as described herein, and those —$R^1$, —$R^2$, —$R^3$, —$R^4$, and —$R^5$ that are not —$NR^8R^9$ are —H. For example, some preferred compounds of the disclosure have the following sub-Formula Ib, wherein $R^6$, $R^7$, and $R^9$, or following sub-Formula Ic, wherein $R^6$ and $R^7$ have the meanings described herein.

Other preferred compounds of Formula I include those wherein one or more of —$R^1$, —$R^2$, —$R^3$, —$R^4$, and —$R^5$ is/are —$NR^6R^7$, and those —$R^1$, —$R^2$, —$R^3$, —$R^4$, and —$R^5$ that are not —$NR^6R^7$ are —H. For example, some preferred compounds of the disclosure have the following sub-Formula Id and Ie, wherein $R^6$ and/or $R^7$ have the meanings described herein.

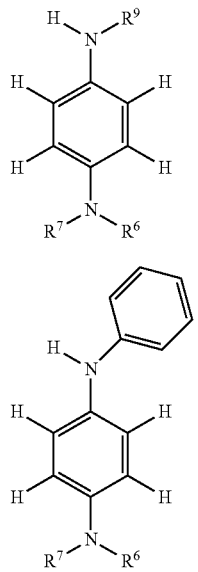

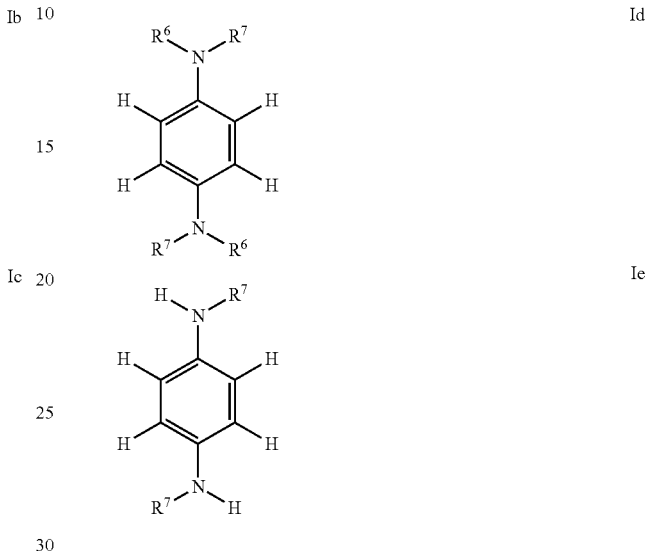

Exemplary compounds of sub-Formula Ic wherein both of $R^6$ and $R^7$ are of the formula: —$(CR^{10}_2)_q(CHOH)(R^{12}O)_zR^{11}$ include, but are not limited to, 1-bis[3-methoxy-2-hydroxy-ethylamino]-4-phenylaminobenzene, 1-bis[3-ethoxy-2-hydroxy-propylamino]-4-phenylaminobenzene, 1-bis[3-propoxy-2-hydroxy-propylamino]-4-phenylaminobenzene, 1-bis[3-butoxy-2-hydroxy-propylamino]-4-phenylaminobenzene, 1-bis[3-pentyloxy-2-hydroxy-propylamino]-4-phenylaminobenzene, 1-bis[3-hexyloxy-2-hydroxy-propylamino]-4-phenylaminobenzene, 1-bis[3-octyloxy-2-hydroxy-propylamino]-4-phenylaminobenzene, 1-bis[3-nonyloxy-2-hydroxy-propylamino]-4-phenylaminobenzene, 1-bis[3-undecyloxy-2-hydroxy-propylamino]-4-phenylaminobenzene, 1-bis[3-dodecyloxy-2-hydroxy-propylamino]-4-phenylaminobenzene, 1-bis[3-tridecyloxy-2-hydroxy-propylamino]-4-phenylaminobenzene, 1-bis[3-tetradecyloxy-2-hydroxy-propylamino]-4-phenylaminobenzene, 1-bis[3-pentadecyloxy-2-hydroxy-propylamino]-4-phenylaminobenzene, 1-bis[3-hexadecyloxy-2-hydroxy-propylamino]-4-phenylaminobenzene, 1-bis[3-heptadecyloxy-2-hydroxy-propylamino]-4-phenylaminobenzene, 1-bis[3-octadecyloxy-2-hydroxy-propylamino]-4-phenylaminobenzene, 1-bis[3-eleyloxy-2-hydroxy-propylamino]-4-phenylaminobenzene, 1-bis[3-nonadecyloxy-2-hydroxy-propylamino]-4-phenylaminobenzene, 1-bis[3-eicosyloxy-2-hydroxy-propylamino]-4-phenylaminobenzene, 1-bis[3-heneicosyloxy-2-hydroxy-propylamino]-4-phenylaminobenzene, 1-bis[3-docosyloxy-2-hydroxy-propylamino]-4-phenylaminobenzene, and 1-bis[3-tricosyloxy-2-hydroxy-propylamino]-4-phenylaminobenzene.

Exemplary compounds of sub-Formula e wherein $R^7$ is of the formula: —$(CR^{10}_2)_q(CHOH)(R^{12}O)_zR^{11}$ include, but are not limited to, 1,4-bis[3-methoxy-2-hydroxy-propylamino]benzene, 1,4-bis[3-ethoxy-2-hydroxy-ethylamino]benzene, 1,4-bis[3-propoxy-2-hydroxy-propylamino]benzene, 4-bis[3-butoxy-2-hydroxy-propylamino]benzene, 1,4-bis[3-pentyloxy-2-hydroxy-propylamino]benzene, 1,4-bis[3-hexyloxy-2-hydroxy-propylamino]benzene, 1,4-bis[3-heptyloxy-2-hydroxy-propylamino]benzene, 1,4-bis[3-octyloxy-2-hydroxy-propylamino]benzene, 1,4-bis[3-nonyloxy-2-hydroxy-propylamino]benzene, 1,4-bis[3-decyloxy-2-hydroxy-propylamino]benzene, 1,4-bis[3-undecyloxy-2-hydroxy-propylamino]benzene, 1,4-bis[3-dodecyloxy-2-hydroxy-propylamino]benzene, 1,4-bis[3-tridecyloxy-2-hydroxy-propylamino]benzene, 1,4-bis[3-tetradecyloxy-2-hydroxy-propylamino]benzene, 1,4-bis[3-pentadecyloxy-2-hydroxy-propylamino]benzene, 1,4-bis[3-hexadecyloxy-2-hydroxy-propylamino]benzene, 1,4-bis[(3-heptadecyloxy-2-hydroxy-propylamino]benzene, 1,4-bis[3-octadecyloxy-2-hydroxy-propylamino]benzene, 1,4-bis[3-eleyloxy-2-hydroxy-propylamino]benzene, 1,4-bis[3-nonadecyloxy-2-hydroxy-propylamino]benzene, 1,4-bis[3-eicosyloxy-2-hydroxy-propylamino]benzene, 1,4-bis[3-heneicosyloxy-2-hydroxy-propylamino]benzene, 1,4-bis[3-docosyloxy-2-hydroxy-propylamino]benzene, and 1,4-bis[3-tricosyloxy-2-hydroxy-propylamino]benzene.

Aromatic compounds of the disclosure that can be used for synthesis of the antioxidant compounds of the disclosure include aminophenol and diamino benzene compounds as described herein, can be prepared using methods according to the disclosure. In some modes of practice, and as a general matter, an aryl-group containing reactant having either (a) a primary amine and a hydroxyl group, such as 4-aminophenol, (b) two primary amine groups, such as 1,4-diaminobenzene (p-phenylenediamine), (c) a primary and a secondary amine group, such as phenylphenylenediamine, or (d) a primary and a tertiary amine group, such as dimethyl-4- phenylenediamine, is reacted with a carbon and oxygen-containing reactant, capable of reaction with the primary (and optionally secondary) amine group to provide a product, such as described herein. The carbon and oxygen-containing reactant, when reacted with the amine group can provide one or both of group(s) $R^6$ and/or $R^7$ which can be of the formula: $—(CR^{10}{}_2)_q(CHOH)(CH_2)_zR^{11}$, or $(CR^{10}{}_2)_q(CHOH)(R^{12}O)_zR^{11}$.

In some modes of practice, the reactant includes an oxirane group or an oxitane group as the amine-reactive group. Oxirane- and oxitane-containing reactants can include desired carbon chemistry and can also include additional oxygen atom(s), such as in the form of ether groups. Exemplary oxirane-containing reactants are glycidyl ethers, such as alkyl glycidyl ethers.

In some modes of practice the oxirane-containing reactant is of Formula II:

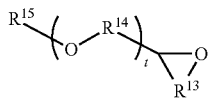

wherein $R^{13}$ is $—(CH_2)—$ or $—(CH_2CH_2)—$, wherein $R^{14}$ is $—(CH_2)_w—$, wherein w is an integer in the range of 1-3, t is an integer in the range of 1-100, 1-50, 1-25, 1-15, 1-10, 1-5, or t is 2, 3, or 4, and wherein $R^{15}$ is $R^{10}$, as described herein, optionally substituted with one or more hydroxyl groups.

Nitrogen- and oxygen-containing aromatic compounds that can be used as antioxidants are also described in commonly-assigned U.S. Provisional Patent Application entitled "Polyhydroxyaminophenol Compounds and Methods for Preventing Monomer Polymerization", and filed concurrently with this application.

In modes of preparation, the aminophenol or diamino benzene compound as described herein can be reacted with the carbon and oxygen-containing reactant, e.g., a glycidyl ether, at a desired molar ratio. The ratio can be an equimolar ratio, or a molar ratio wherein the carbon and oxygen-containing reactant is greater than the aminophenol or diamino benzene compound. In exemplary modes of practice the carbon and oxygen-containing reactant is reacted at about a two molar excess over the aminophenol or diamino benzene compound.

In some modes of practice the aryl-group containing reactant and carbon and oxygen-containing reactant (e.g., oxirane or oxitane-containing reactant) are reacted at a temperature where one or both reactants are in the liquid phase. In some modes of practice, the oxirane/oxitane-containing reactant is in the liquid phase at the desired reaction temperature, and it solvates the aryl-group containing reactant. In this regard, the aryl-group containing reactant can have a melting point greater than the carbon and oxygen-containing reactant. In embodiments wherein the reactants are melted and/or solvated at the desired reaction temperature, any other component, such as an organic solvent otherwise typically used in reaction schemes, may be optional, and not required. Therefore, an organic solvent can be excluded from the reaction method. Further, a component such as a catalyst can also be optional, and therefore not required. In some modes of practice, the synthesis method does not include use of (a) an organic solvent, (b) a catalyst, or both (a) and (b).

Exemplary reaction temperatures can be in the range of about room temperature (~25° C.) to about 250° C., about 40° C. to about 200° C., or about 50° C. to about 175° C.

Alternatively, the aryl-group containing and carbon and oxygen-containing reactants can be reacted in an organic solvent such as an alcohol like methanol, butyl carbitol, and butyl glycol, with reflux at an elevated temperature (e.g., >100° C.).

A composition that includes the oxygenated aromatic amine and any one or more optional component can be in a desired form, such as in a liquid form, a dry form, or as a suspension or dispersion. The oxygenated aromatic amine can be in a desired physical state in the composition, such as in a dissolved state, in a partially dissolved state, in a suspended state, or in a dry mixture. The oxygenated aromatic amine can optionally be in particulate forms in the composition. If the oxygenated aromatic amine is in a particulate form, the particles can optionally be described in terms of particle size (e.g., particles of a size range) and/or shape. The form of the composition and the state of the component(s) therein can be chosen by selection of the oxygenated aromatic amine, with an understanding of its physical properties.

The form of the composition and the state of the component(s) therein can also be affected by the inclusion of one or more optional components, such as a solvent, or solvent mixture, or other excipient compounds that are different than the oxygenated aromatic amine. The form of the composition and the state of the components therein can also be affected by temperature, and composition properties may optionally be described in circumstances at a particular temperature (e.g., at a storage temperature such as 5° C. or below, at room temperature (25° C.), or at a temperature used for the desired application.

As noted, an oxygenated aromatic amine-containing composition can include other components such as a solvent, surfactants, dispersants, etc. If an optional component is present in the composition, it may be described in terms of a weight amount relative to the oxygenated aromatic amine. The optional component(s) may be present in a weight amount greater than, in an amount about the same as, or an amount less than the oxygenated aromatic amine.

As used herein, the term "optional" or "optionally" means that the subsequently described object (e.g., compound), event (e.g., processing step), or circumstance may, but need not occur, and that the description includes instances where the object, event, or circumstance occurs and instances in which it does not.

Compositions of the disclosure can include those recited compounds and optionally can include other components in the composition but in very small amounts (e.g., described in terms of a composition "consisting essentially of" the recited components). For example, such compositions can include one or more other components but not in an amount that is greater than about 1% (wt), greater than about 0.5% (wt), greater than about 0.1% (wt), or greater than about 0.01% (wt), of the total composition. A composition that consists essentially of a solid component that is the oxygenated aromatic amine (for example, dissolved in a solvent) can optionally include one or more other (e.g., solid) components but in an amount less than about 1% (wt) of the total composition weight. In a composition "consisting of" the recited components there is no other measurable amount of component other than the recited component. In some embodiments, an oxygenated aromatic amine can optionally be present in an amount of less than 1% (wt), less than 0.5% (wt), less than 0.1% (wt), or less than 0.01% (wt), of the total composition.

As used herein, the terms "substantially" and "consisting essentially of" modifying, for example, the type or quantity of an ingredient in a composition, a property, a measurable quantity, a method, a position, a value, or a range, employed in describing the embodiments of the disclosure, refers to a variation that does not affect the overall recited composition, property, quantity, method, position, value, or range thereof in a manner that negates an intended composition, property, quantity, method, position, value, or range. Examples of intended properties include, solely by way of non-limiting examples thereof, dispersibility, stability, rate, solubility, and the like; intended values include weight of a component added, concentration of components added, and the like. The effect on methods that are modified include the effects caused by variations in type or amount of materials used in a process, variability in machine settings, the effects of ambient conditions on a process, and the like wherein the manner or degree of the effect does not negate one or more intended properties or results; and like proximate considerations. Where modified by the term "substantially" or "consisting essentially of", the claims appended hereto include equivalents to these types and amounts of materials.

As used herein, the term "about" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. Further, where "about" is employed to describe any range of values, for example "about 1 to 5" the recitation means "1 to 5" and "about 1 to about 5" and "1 to about 5" and "about 1 to 5" unless specifically limited by context.

An amount of the oxygenated aromatic amine, and any other (optional) component in a composition can be described in various ways, such as by a weight percentage (% wt.) or by molar amount of oxygenated aromatic amine in the composition. When other components are used along with the oxygenated aromatic amine, such compounds can also be described in terms of weight ratios, or in terms of relative amounts to one another, in a composition.

The oxygenated aromatic amine can be present in a composition with a solvent, or a combination of solvents. A solvent or solvent combination can be chosen so that the oxygenated aromatic amine is soluble in the solvent or solvent combination. If the nitrogen- and oxygen-containing aromatic antipolymerant is a liquid at ambient conditions, a miscible solvent can be chosen.

Useful solvents include any solvent in which the oxygenated aromatic amine is soluble or can be stably suspended. In some embodiments, a solvent or solvent combination can be selected from water soluble or water miscible solvents such glycol-based solvents and hydrophobic or hydrocarbon solvents such as aromatic solvents, paraffinic solvents, or mixtures of both.

Exemplary glycol solvents include, but are not limited to, $C_1$-$C_8$ glycols such as ethylene glycol, propylene glycol, diethylene glycol, and triethylene glycol, ethers of such glycols such as diethylene glycol monobutyl ether, diethylene glycol monomethyl ether, diethylene glycol monoethyl ether, diethylene glycol monobutyl ether, triethylene glycol, triethylene glycol monomethyl ether, liquid polyethylene glycol, dipropylene glycol, dipropylene glycol monomethyl ether, dipropylene glycol monoethyl ether, and a low molecular weight polypropylene glycol and the like and combinations thereof. Commercial solvents such as Butyl Carbitol and Butyl CELLOSOLVE™, which contains primarily Butyl CARBITOL™, which consists primarily of ethylene glycol monobutyl ether may be used and are available from DOW.

Other exemplary hydrophobic or hydrocarbon solvents include heavy aromatic naphtha, toluene, ethylbenzene, isomeric hexanes, benzene, xylene, such as ortho-xylene, para-xylene, or meta-xylene, and mixtures of two or more thereof.

In some embodiments, the solvent is selected from glycol and aromatic naphtha and combinations thereof.

The amount of oxygenated aromatic amine (with one or more optional components), in a solvent, or a combination of solvents, can be described one or more ways, such as by the percent solids (wt) of the component(s) in the composition, or by the molar amount of solid components in the composition.

As an example, a stock composition of oxygenated aromatic amine can be dissolved in a solvent to a concentration of about at least about 0.00001% (wt), at least about 5% (wt), such as in an amount in the range from about 0.00001% (wt) to about 50% (wt).

In some modes of practice, the oxygenated aromatic amines of the disclosure can be used as antioxidants. Oxygenated aromatic amine antioxidants of the disclosure can be used to retard the oxidation of an organic substance in a composition. Oxidation is a chemical reaction that can produce free radicals, thereby leading to reactions that may otherwise form undesirable products in the composition or change the properties of the composition in an unwanted matter.

In some modes of practice the oxygenated aromatic amine acts as an antioxidant to prevent fouling in a composition that includes an organic compound. The term "fouling" refers to the formation of polymers, prepolymers, oligomer and/or other materials which would become insoluble in and/or precipitate from a stream and deposit on equipment under conditions of operating the equipment. In turn, the oxygenated aromatic amine can be referred to as an "antifoulant" as it prevents or reduces such formation.

The oxygenated aromatic amine antioxidant can be used in conjunction with compositions containing organic compounds and "process equipment" such as reactors, reactor beds, pipes, valves, distillation columns, trays, condensers, heat exchangers, compressors, fans, impellers, pumps, recirculators, inter-coolers, sensors, and the like, that are associated with the process and which may be subject to fouling by oxidation of organic components therein. This term also includes sets of these components where more than one of the components is part of a "system."

In some modes of practice, a composition of the disclosure with nitrogen- and oxygen-containing aromatic antipolymerant and solvent (e.g., glycol) is used with a process that involves a distillation tower that is used to separate and purify organic compounds, such as vinylic monomers. For example, in art-known processes ethylbenzene can be subjected to a catalytic dehydrogenation reaction which results in the formation of styrene. The reaction product containing styrene also contains other compounds such as aromatics like toluene and benzene, unreacted ethylbenzene, and other materials such as polymers. This mixture of compounds is generally fractionally distilled using one or more distillations towers. Typically, heat is used to help separate the components in the distillation tower. Following distillation the fractionated components can be separated into pure product streams with higher purity. Optionally, the oxygenated aromatic amine antioxidant is used along with one or more secondary components such as stabilizers like butylated hydroxytoluene (BHT) and tert-butylcatechol (TBC). In an exemplary mode of practice these components are used in a distillation tower that is used to separate and purify vinylic monomers.

An oxygenated aromatic amine-containing composition can be introduced into a stream leading from the reaction bed to the distillation tower, or can be directly added to the distillation tower. The compositions can be added prior to heating the monomer composition or while heating the monomer composition in the distillation tower. In embodiments, the oxygenated aromatic amine has a boiling point that is higher than that of the desired compound or distillate (e.g., a monomer such as styrene) subject to distillation tower and during the distillation process the desired compound is separated from the oxygenated aromatic amine compound by virtue of temperature difference. In embodiments, the boiling point difference between the compound of interest and the oxygenated aromatic amine is about 10° C. or greater, about 15° C. or greater, about 20° C. or greater, about 25° C. or greater, about 30° C. or greater, about 35° C. or greater, about 40° C. or greater, about 45° C. or greater, or about 50° C. or greater.

Alternatively, or in addition to adding the oxygenated aromatic amine during a distillation process, the composition can be optionally or further added to a distillation effluent stream, such as a purified styrene stream. Optionally, another antioxidant can be added to a distillation effluent stream prior to or along with the oxygenated aromatic amine antioxidant.

The oxygenated aromatic amine, optionally used in combination with one or more other components, can be used with any "hydrocarbon process stream" which can include unsaturated monomer in order to stabilize the stream during transportation and storage. In some modes of practice, the oxygenated aromatic amine can be used in conjunction with a "petroleum product" which refers to any hydrocarbon product obtained from a subterranean reservoir, any product derived therefrom, or any mixture thereof. Polymerizable monomers are found in or can be chemically derived from petroleum products. Nonlimiting examples of petroleum products include but are not limited to crude oil, reduced crude oil, crude distillate, heavy oil, or bitumen, hydrotreated oil, refined oil, byproducts of petroleum product processing such as pyrolysis, hydrotreating, or phase separation, or mixtures of two or more of these. A liquid petroleum product is a petroleum product that is substantially a liquid at 20° C.

The oxygenated aromatic amine can be added to or can be present in a "petroleum process stream" which refers to any petroleum product disposed within petroleum process equipment in fluid contact with an interior surface thereof.

The petroleum process stream can include, or can be capable of forming as a by-product, a compound that is oxidized to an unwanted material. The process stream may be substantially static, such as a petroleum product disposed within in a settler (separator) or storage container for a selected period of contact, such as up to two years. The process stream may be substantially dynamic, such as a liquid petroleum product disposed within a pipe during transportation of the product from a first location to a second location. In some embodiments the process stream includes one or more additional components related to petroleum processing; such components are not particularly limited.

"Petroleum process equipment" or "petroleum process apparatus" refers to a man-made item having an interior surface including a metal, further wherein one or more petroleum products are fluidly contacted with the metal for any period of time and at any temperature further as determined by context. Petroleum process equipment includes items for removing petroleum products from a subterranean reservoir, for transporting one or more petroleum products from a first location to a second location, or for separating, refining, treating, isolating, distilling, reacting, metering, heating, cooling, or containing one or more petroleum products.

In embodiments, compositions including the oxygenated aromatic amine are thermally stable and have antioxidant activity in processing streams at temperatures of about 20° C. to about 400° C., for example about 100° C. to 400° C., or about 100° C. to 350° C., or about 100° C. to 300° C., or about 100° C. to 250° C., or about 100° C. to 200° C., or about 100° C. to 150° C.

In embodiments, compositions including oxygenated aromatic amine can be introduced into a composition with an organic compound, such as a liquid petroleum process stream in a batch-wise, a continuous, or a semi-continuous manner. In some embodiments, the oxygenated aromatic amine (and any other optional component) is introduced manually; and in other embodiments, their introduction is automated. In embodiments, the amount of the oxygenated aromatic amine is introduced over a selected unit of time is varied with a variable composition of the associated process stream. Such variability in dosing may be conducted manually by periodic testing of the process equipment interior surfaces, following by adjusting the amount of the composition up or down based on test results; or automatically by monitoring of one or more conditions within the interior of the petroleum process equipment and signaling the need to apply more composition to the process stream.

In some embodiments, the oxygenated aromatic amine antioxidant is added to a petroleum product that is a crude oil, a reduced crude oil, a heavy oil, a bitumen, a coker charge, a hydrotreater influent, a hydrotreater effluent, a flashed crude, a light cycle oil, or a diesel or naphtha refinery stream. Accordingly, the antioxidant can be used to treat refinery reactant streams that are prone to oxidation. In embodiments, the oxygenated aromatic amine is added to petroleum process equipment conventionally associated with the collecting, processing, transportation, or storage of one or more of crude oil, reduced crude oil, crude distillate, heavy oil, bitumen, coker charge, flashed crude, light cycle oil, or a diesel or naphtha refinery stream, including pipes and associated infrastructure used to fluidly connect process equipment items together to facilitate processing of a process stream disposed therein. The antioxidant can be added to naphtha products more specifically described herein.

The antioxidant can be used to treat reactive naphtha products with varying levels of reactivity. Levels of reactivity in naphtha products can vary due to different levels of unsaturation in the product. Naphtha products obtained from different refineries can display different levels of reactivity, and such reactivity can be determined using a bromine test.

Equipment treated with the oxygenated aromatic amine and any other optional component can result in reduction or elimination of fouling interior surface of the equipment. In embodiments, fouling is measured as a relative increase in retention of solids within the treated composition compared to the retention of solids in untreated composition over the same time period. In embodiments, fouling is measured as a relative decrease in the weight or volume of precipitate arising from a selected period of contact of a treated process stream in an associated process equipment item, relative to the same period of contact of the process equipment with the corresponding untreated process stream. Stated differently, a reduction in fouling is a relative decrease in the measured weight or volume of solids deposited on or precipitated from process equipment contacted with the treated process stream over a selected period of time, when compared to the weight or volume of solids deposited or precipitated from an untreated process stream over the same period of time.

The oxygenated aromatic amine can also inhibit unwanted fouling of the process equipment in a primary fractionation process, light ends fractionation, non-aromatic halogenated vinyl fractionation and stabilization, process-gas compression, dilution steam system, caustic tower, quench water tower, quench water separator (pyrolysis gasoline), butadiene extraction, propane dehydrogenation, diesel and petrol fuel stabilization, olefin metathesis, styrene purification, hydroxyhydrocarbon purification, and stabilization of compositions during transportation and storage.

The oxygenated aromatic amine can be added at any given point in a process and at one or more locations. For example, an antipolymerant composition can be added directly at the interstage coolers or compressors or upstream of the inter-coolers or compressors. The oxygenated aromatic amine can be added continuously or intermittently to the process equipment as required preventing or reducing fouling.

The oxygenated aromatic amine can be introduced to desired systems by any suitable method. For example it may be added in neat or a dilute solution. In some embodiments, a composition containing the oxygenated aromatic amine can be applied as a solution, emulsion, or dispersion that is sprayed, dripped, poured or injected into a desired opening within a system or onto the process equipment or process condensate. In some embodiments, the composition may be added with a washoil or an attemperation water.

After introducing the oxygenated aromatic amine to process equipment, treated process equipment can be observed to have less deposition on equipment than in process equipment without addition of the composition. Reduction or prevention in fouling can be evaluated by any known method or test. In some embodiments, the reduction or prevention of fouling can be accessed by measuring the time it takes for a sample with and without the antifoulant composition to gel.

In other embodiments, an oxygenated aromatic amine antioxidant of the disclosure is added to a fuel or a lubricant. The antioxidant can inhibit oxidation of organic components in the fuel or lubricant thereby preventing formation of undesirable components that can lead to reduced performance, malfunctioning, or damage of equipment, such as engines, that use the fuel or lubricant. In some modes of practice, the oxygenated aromatic amine antioxidant can be used in a conveyor lubricant to facilitate movement of a conveyor belts made of stainless steel or plastic.

Oxygenated aromatic amine antioxidant of the disclosure can be added to low-temperature oils, jet fuels and gasolines, including aviation gasolines, turbine oils, transformer oils, hydraulic fluids, waxes, and industrial greases in industrial use.

The antioxidants of the disclosure can improve gasoline-based fuels that are stored for a prolonged period of time, which would otherwise deteriorate because of polymerization and oxidation reactions in the gasoline composition. The process of gasoline-based fuel degradation can be complex because of the various hydrocarbons present in the composition. For example, the antioxidants of the disclosure can prevent the formation of gums and darkening of color in darkening of gasoline composition when stored for extended periods of time.

Compounds with unsaturation, like olefins and dienes, are susceptible to oxidation and polymerization when oxygen is present. These unsaturated compounds may occur in fuel compositions due to secondary refining operations and blending of hydrocarbon streams from thermal processes. Other non-organic contaminants in hydrocarbon compositions such as copper can promote formation of peroxides in the composition and can lead to polymerization reactions. Copper contamination may arise to contact of a hydrocarbon composition with equipment used to transport, store, or refine hydrocarbon materials. Copper may also be introduced to refining chemicals used in the refining and the fuel system of vehicles.

The oxygenated aromatic amine antioxidant can be used in gasoline fuel containing cracked components obtained from various secondary processing operations, such as Fluidized Catalytic Cracking (FCC), VB and Coker. The antioxidant of the disclosure can improve fuel properties by preventing oxidation, preventing sediment formation, and increasing corrosion inhibition and water uptake.

The oxygenated aromatic amine antioxidant can be added to a gasoline composition, such as one derived from petroleum and that includes mainly hydrocarbons. Typical uses are gasolines as internal combustion engines fuels.

Gasoline hydrocarbons typically have five to twelve carbon atoms, and typically have higher octane levels. Octane ratings of about 85% or greater, about 86% or greater, about 87% or greater, about 88% or greater, about 89% or greater, about 90% or greater, about 91% or greater, about 92% or greater, or about 93% or greater are common commercially-available preparations. Octane rating of gasoline is typically measured relative to a mixture of isooctane (i.e., 2,2,4-trimethylpentane) and n-heptane by running the fuel samples through a specific test engine with a variable compression ratio under controlled conditions. For example, 93-octane gasoline typically has the same octane rating as a mixture of 93% (v/v) isooctane and 7% (v/v) n-heptane. A typical gasoline may include a mixture of paraffins, naphthenes, aromatics, and olefins.

The oxygenated aromatic amine antioxidant can be added to gasoline blends, such as blends of gasoline and ethanol. In ethanol mixtures, ethanol may be present in a gasoline ethanol mixture in any desired amount ranging from 0.1% (vol) to 99% (vol.). More specific ethanol-gasoline blends can have 1-5% (vol.) ethanol, 5-10% (vol.) ethanol, 10-15% (vol.) ethanol, 15-20% (vol.) ethanol, 20-25% (vol.) ethanol, 25-30% (vol.) ethanol, 30-40% (vol.) ethanol, 40-50% (vol.) ethanol, 50-60% (vol.) ethanol, 60-70% (vol.) ethanol, 70-80% (vol.) ethanol, 80-90% (vol.) ethanol, or 90-99% (vol.) ethanol, the remaining portion being gasoline.

The antioxidant of the disclosure can be used with pyrolysis gasoline (Pygas) or a pyrolysis gasoline product. Pyrolysis gasoline is a naphtha-based product having a high octane number mixture and includes olefins, paraffins, and aromatics. pyrolysis gasoline can be produced as a by-product of high temperature naphtha cracking in a process that produces ethylene and propylene. The antioxidant can be used with pure pyrolysis gasoline, or the antioxidant can be added to a pyrolysis gasoline blend, such as a blend that includes other hydrocarbon preparations, or ethanol. Antioxidant s of the disclosure can be added to a distilled pyrolysis gasoline product, such as distilled using a BTX process which separates pyrolysis gasoline) to separate it into its components, including benzene.

Antioxidants of the disclosure can be introduced into a gasoline product at any suitable location. For example, for addition to pyrolysis gasoline, which is typically processed through a hydrotreater prior to being blended with other gasolines to form motor gasoline, and antioxidant can be introduced into the gasoline upstream or downstream of the hydrotreater, such as before the pyrolysis gasoline is mixed with other gasolines.

The antioxidant can be used at a desired concentration in the gasoline product. Exemplary amounts of the oxygenated aromatic amine antioxidant in the gasoline product are in the range of about 1 ppm to about 5000 ppm, about 2.5 ppm to about 2500 ppm, about 5 ppm to about 1500 ppm, about 7.5 ppm to about 1250 ppm, about 10 ppm to about 1000 ppm, about 50 ppm to about 1000 ppm, about 100 ppm to about 1000 ppm, about 250 ppm to about 1000 ppm, about 50 ppm to about 750 ppm, about 100 ppm to about 500 ppm, or about 250 ppm to about 500 ppm.

The oxygenated aromatic amine antioxidant can be used as the sole antioxidant for treating compositions that have an organic compound, or can be used as an antioxidant with one or more other antioxidants in a treatment composition. For example, the oxygenated aromatic amine antioxidant can be the primary antioxidant in a treatment composition, such as in an amount greater than 50% (wt), about 60% (wt) or greater, about 70% (wt) or greater, about 80% (wt) or greater, about 90% (wt) or greater, about 95% (wt) or greater, about 99% (wt) or greater of antioxidants in a treatment composition.

The oxygenated aromatic amine antioxidant, or mixture of antioxidants, can be used in neat form or in a solvent such as aromatic solvents.

The addition of the antioxidant of the disclosure can provide a gasoline product with increased oxidative stability resulting in lower gum formation.

A test to determine antioxidant efficacy is the Induction Period Test according to ASTM D-525/IP: 40, in which measured quantity of fuel (50 mL) is oxidized under certain condition in a container including gasoline and the antioxidant. The test is run starting at a desired temperature, such as in the range of 95-150° C., at a desired feed rate (depending on reactivity), and having oxygen at a pressure of about 100 psi. The pressure is read at stated intervals or recorded continuously until the break is reached. The time required for the sample to reach this point is observed and reported as the induction period.

Other tests can be used to assess the quality of fuels that are to be treated with antioxidants of the disclosure. Another test measures the presence of existent gum in a fuel composition. For example, ASTM D-381/IP: 131, 2, takes a quantity of fuel (50 mL) and evaporates it under controlled temperature and air flow conditions. The resulting residue is weighed and reported as $gm/m^3$. This test can be performed to understand how much gum is already present in a gasoline sample, and can be factored into the accelerated aging test.

Another test is an ambient aging test. A standard ambient aging test is done for three months. For example, in such a test, a 400 mL sample of antioxidant-containing gasoline is stored in 500 mL borosilicate glass bottles for three months at ambient temperatures in triplicate. After completion of the first, second and third months one set is subjected to the Existent Gum test as per ASTM D-381 and the result reported as gm/mi. Color of the fuel is also noted after completion of each month.

The oxygenated aromatic amine antioxidant can be tested with a desired selection of components, tested under selected conditions, such as time and temperature, and using selected gasoline compositions.

The oxygenated aromatic amine antioxidant can be tested for its ability to affect the water tolerance characteristics of gasoline, or the ability to change fuels properties to prevent rusting of ferrous parts when fuel comes in contact with water.

For example, in fats and oils, antioxidants delay the onset of oxidation or slow the rate of oxidizing reactions. Fats and oils commonly spoil as oxidation of the lipids cause production of compounds that lead to different odors and taste and continue to affect other molecules in the food. These foods spoil due to exposure to oxygen and sunlight that lead to oxidation of food. Accordingly, an oxygenated aromatic amine antioxidant of the disclosure can be added to a food product to inhibit oxidation of one or more components of the food product.

Exemplary food products can include an oxygenated aromatic amine antioxidant of the disclosure include, but are not limited to, fermented beverages such as wine and malt-based fermented beverages such as beer and beer-like beverages; foods that are high in protein and/or fat content, such as dairy products like milks, yogurts, cheeses, ice cream; half-and-half; whipping cream; food preparations that are oil- or fat-based, such as vegetable oils, butter products, spreads, margarine, shortening, and the like; baked products such as biscuits, muffins, waffles, pancakes, breads, cookies, and pastries; cereals, cereal-based products; granola; muesli; jams, jellies, marmalades, fruit preserves, fruit-based juices, fruit juice concentrates, fruit-based puree; canned and pureed vegetables; processed meat products such as ground beef, ground chicken, ground pork, and sausages; chocolates, candies, and chewing gums.

Exemplary concentrations of the oxygenated aromatic amine antioxidants of the disclosure present in food products are in the range of about 1 ppm to about 500 ppm, or about 1 ppm to about 50 ppm.

The oxygenated aromatic amine antioxidants of the disclosure can also be added to cosmetics and pharmaceutical preparations.

In other embodiments, an oxygenated aromatic amine antioxidant of the disclosure is added to a polymer composition. The polymer composition can be one such as a plastic, a rubber, or an adhesive composition. Antioxidants of the disclosure can prevent oxidative damage of polymer components in the composition, with would otherwise result in loss of strength and flexibility of the composition. For example, polymer breakdown via oxidation can lead to ozonolysis or cracking.

Polymer compositions that are natural rubbers, diene-containing polymers such as polybutadiene, and other rubbers with unsaturation can suffer significant damage by ozone cracking and therefore can benefit from inclusion of the oxygenated aromatic amine antioxidant. Other polymers that are susceptible to oxidation include polypropylene and polyethylene.

Exemplary concentrations of the oxygenated aromatic amine antioxidants of the disclosure present in polymer compositions are in the range of about 100 ppm to about 5% (wt).

Example 1

Synthesis of 4-aminophenol-butylglycidal ether (BGE)

To a 250 mL three necked round-bottom flask equipped with temperature probe, nitrogen inlet, condenser and magnetic stir bar was added butylglycidal ether. 4-aminophenol was then added to the well-stirred reaction mixture. Table 1 also provides the amount of each chemical added and chemical properties. The resulting suspension was heated to 120° C. under nitrogen blanket and stirred for 8 h or until completion of reaction. As reaction proceeded to completion, suspension got converted to a homogenous dark-amber product. The resulting product was characterized by NMR and ESI-MS.

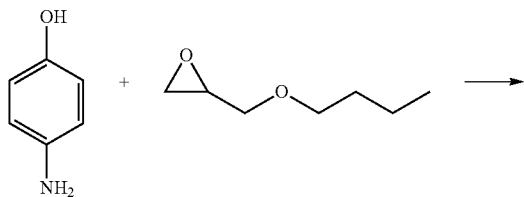

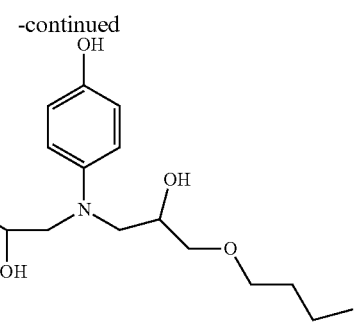

TABLE 1

| | MW(g/mol) | Purity | Amount (g) | n(moles) | Mole ratio |
|---|---|---|---|---|---|
| 4-Aminophenol | 109.12 | 98% | 20 | 0.179619 | 1 |
| BGE | 130.18 | 95% | 49.2 | 0.359041 | 2.00 |

Examples 2-13

Synthesis of Oxygen Aromatic Amines

Using a procedure similar to Example 1, various oxygenated aromatic amines were generated using different starting amine and epoxide reactants, at varying molar ratios. 4-aminophenol, phenylenediamine, and N-phenyl-phenylenediamine were used as amine reactants, and 2-ethylhexylglycidal ether and butyglycidal ether were used as epoxide reactants. The amine to epoxide mole ratio was varied.

TABLE 2

| Sample ID | Amine | Epoxide | Amine:Epoxide mole ratio | Example in FIGS. 1-4 |
|---|---|---|---|---|
| AO-1 | Phenylenediamine | 2-ethylhexylglycidal ether | 1:3 | Ex 2 |
| AO-2 | N-phenyl-phenylenediamine | 2-ethylhexylglycidal ether | 1:1.5 | Ex 3 |
| AO-3 | Phenylenediamine | 2-ethylhexylglycidal ether | 1:2 | Ex 4 |
| AO-4 | N-phenyl-phenylenediamine | 2-ethylhexylglycidal ether | 1:2 | Ex 5 |
| AO-5 | N-phenyl-phenylenediamine | 2-ethylhexylglycidal ether | 1:1 | Ex 6 |
| AO-6 | N-phenyl-phenylenediamine | Butylglycidal ether | 1:2 | Ex 8 |
| AO-7 | 4-aminophenol | 2-ethylhexylglycidal ether | 1:2 | Ex 9 |
| AO-8 | 4-aminophenol | Butylglycidal ether | 1:2 | Ex 10 |
| AO-9 | Phenylenediamine | Butylglycidal ether | 1:3 | NT |
| AO-10 | Phenylenediamine | Butylglycidal ether | 1:2 | NT |
| Comparative Antioxidants | | | | |
| | Type | | | |
| CAO-1 | Phenylenediamine (formulation #1) | | | Ex 7 |
| CAO-2 | Phenylenediamine (formulation #2) | | | Ex 11 |
| CAO-3 | Hindered (tertiary) phenol/Phenylenediamine Blend | | | Ex 12 |
| CAO-4 | Hindered (tertiary) phenol | | | Ex 13 |

Beneficially, the synthesis method provides a readily customizable approach to preparing oxygenated aromatic amines with desired oxygen-containing chemistries attached to one or more amine groups of the compound.

As provided in Table 2, examples of oxygenated aromatic amines were designated AO-1 to AO-10, and correlating to Examples 2-6 and 8-10 for AO-1 to AO-8, which were tested for their antioxidant performance as described herein and as shown in FIGS. 1-4. AO-9 and AO-10 were not tested. Comparative antioxidants (CAO-1-4) including phenylene-diamine (PDA), hindered (tertiary) phenol, and a PDA/hindered (tertiary) phenol blend were along with antioxidants of the disclosure and as also shown in FIGS. 1-4.

Example 14

Antioxidant Performance Testing/Oxidation Stability Test—Heavy Coker Naphtha

To demonstrate the effectiveness of compounds of the disclosure to stabilize reactive naptha samples, heavy coker naphtha from various refineries was used. Solutions of various oxygenated aromatic amines according to Examples 2-13 were prepared in heavy aromatic naphtha and tested according to the ASTM D525 method. The ASTM D525 method covers the determination of the stability of gasoline in finished form, under accelerated oxidation conditions. In accordance with this method, a naphtha sample is placed in a pressure vessel equipped with digital manometer along with the candidate oxygenated aromatic amines. The pressure vessel is closed and oxygen is introduced into the vessel through a Schrader-type valve fitting until an over-pressure of about 689.5 kPa (100 psig) is attained. The vessel is then heated in a oil bath or dry bath to about 100° C. until a drop in pressure is noted signifying a loss of antioxidant activity. The period of time elapsing until a pressure drop is indicated is known as the "break point," with longer induction times signifying increased stabilizer efficacy of the candidate treatment. In this example, the oxygenated aromatic amines antioxidants were used at 500 ppm.

Oxygenated aromatic amines compounds of the disclosure displayed antioxidant properties that were at least as good as, and in many instances, superior to other commercially available or art-known antioxidants (e.g., see CAO-1-4).

Results are shown in FIG. 1.

Example 15

Antioxidant Performance Testing/Oxidation Stability Test—Heavy Coker Naphtha

Figure 2:
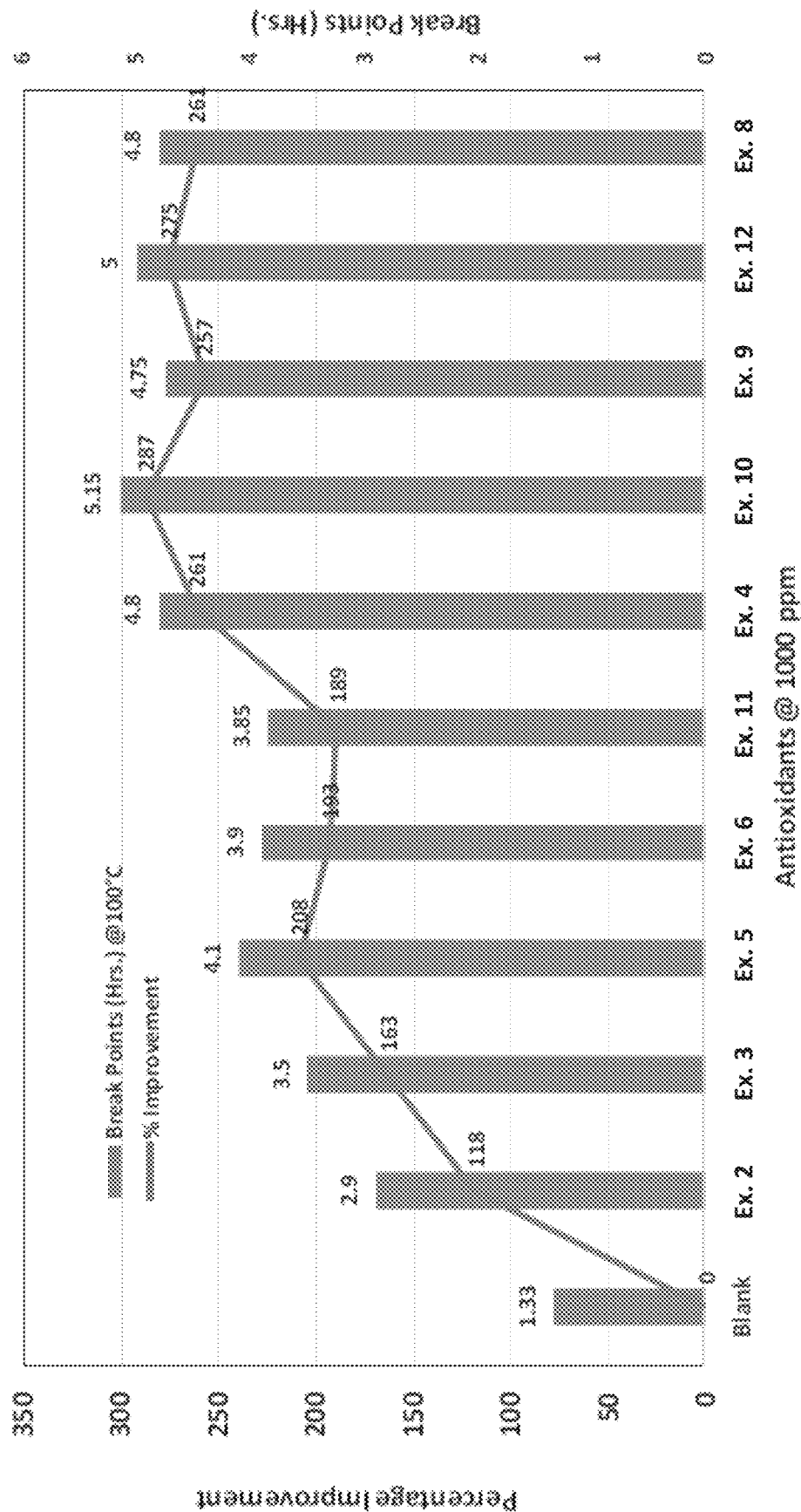
FIG. 2 is a graph of the duration (hours) until reaching pressure break points as determined from antioxidant testing of various oxygenated aromatic amines of the disclosure with heavy coker naphtha.

The effectiveness of compounds of the disclosure to stabilize coker naphtha, solutions of various oxygenated aromatic amines according to Examples 2-13 were prepared in heavy aromatic naphtha and tested according to the ASTM D525 method, as described in Example 14. In this example, the oxygenated aromatic amines antioxidants were used at 1000 ppm. Results are shown in FIG. 2.

Example 16

Antioxidant Performance Testing/Oxidation Stability Test—DCU-1 Coker Naphtha

The effectiveness of compounds of the disclosure to stabilize Delayed Cooking Unit (DCU-1) coker naphtha, solutions of various oxygenated aromatic amines according to Examples 2-13 were prepared in heavy aromatic naphtha and tested according to the ASTM D525 method, as described in Example 14. In this example, the oxygenated aromatic amines antioxidants were used at 250 ppm.

Figure 3:
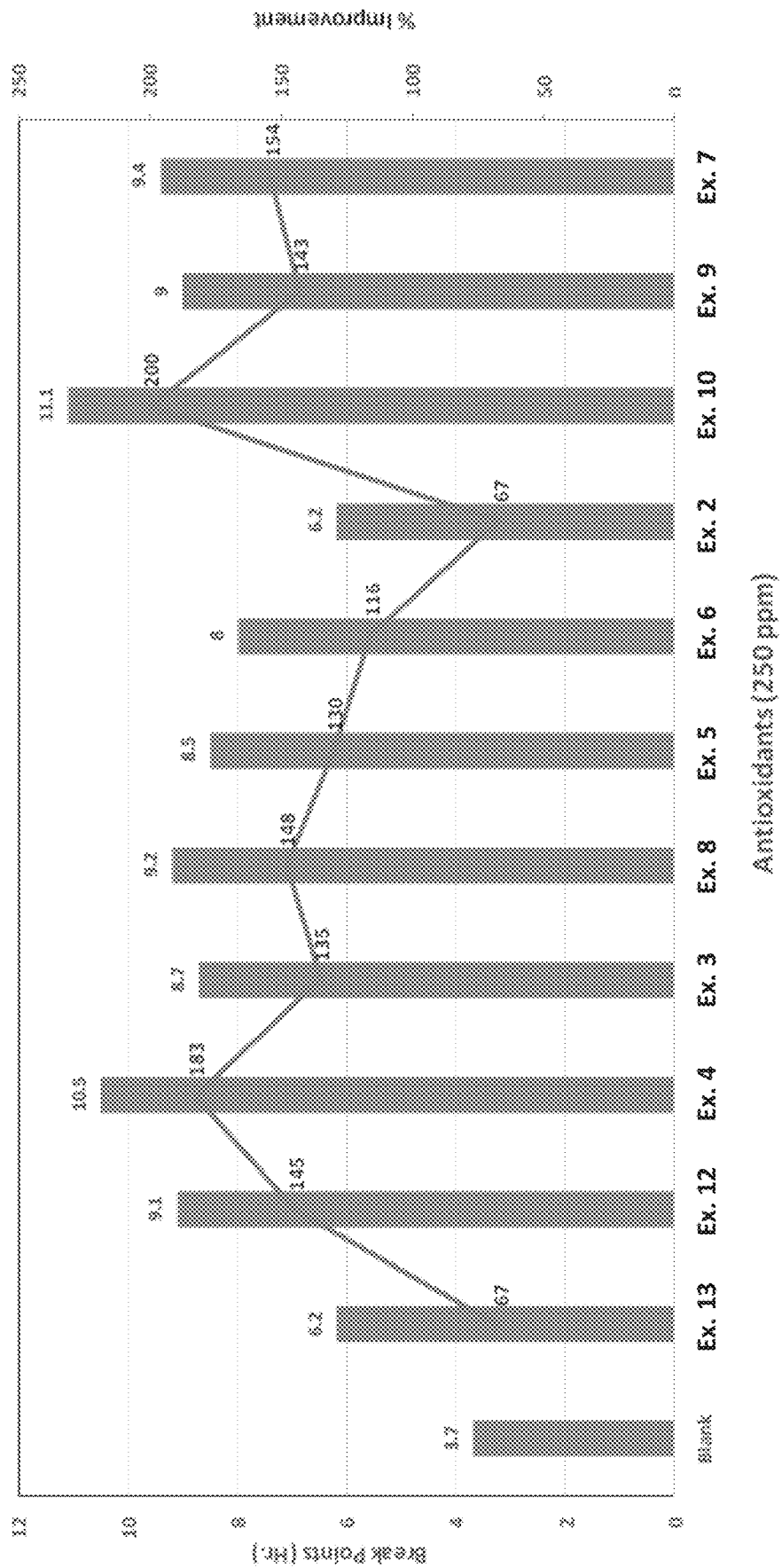
FIG. 3 is a graph of the duration (hours) until reaching pressure break points as determined from antioxidant testing of various oxygenated aromatic amines of the disclosure with DCU-1 coker naphtha.

Results are shown in FIG. 3.

Example 17

Antioxidant Performance Testing/Oxidation Stability Test—Heavy Coker Naphtha

Figure 4:
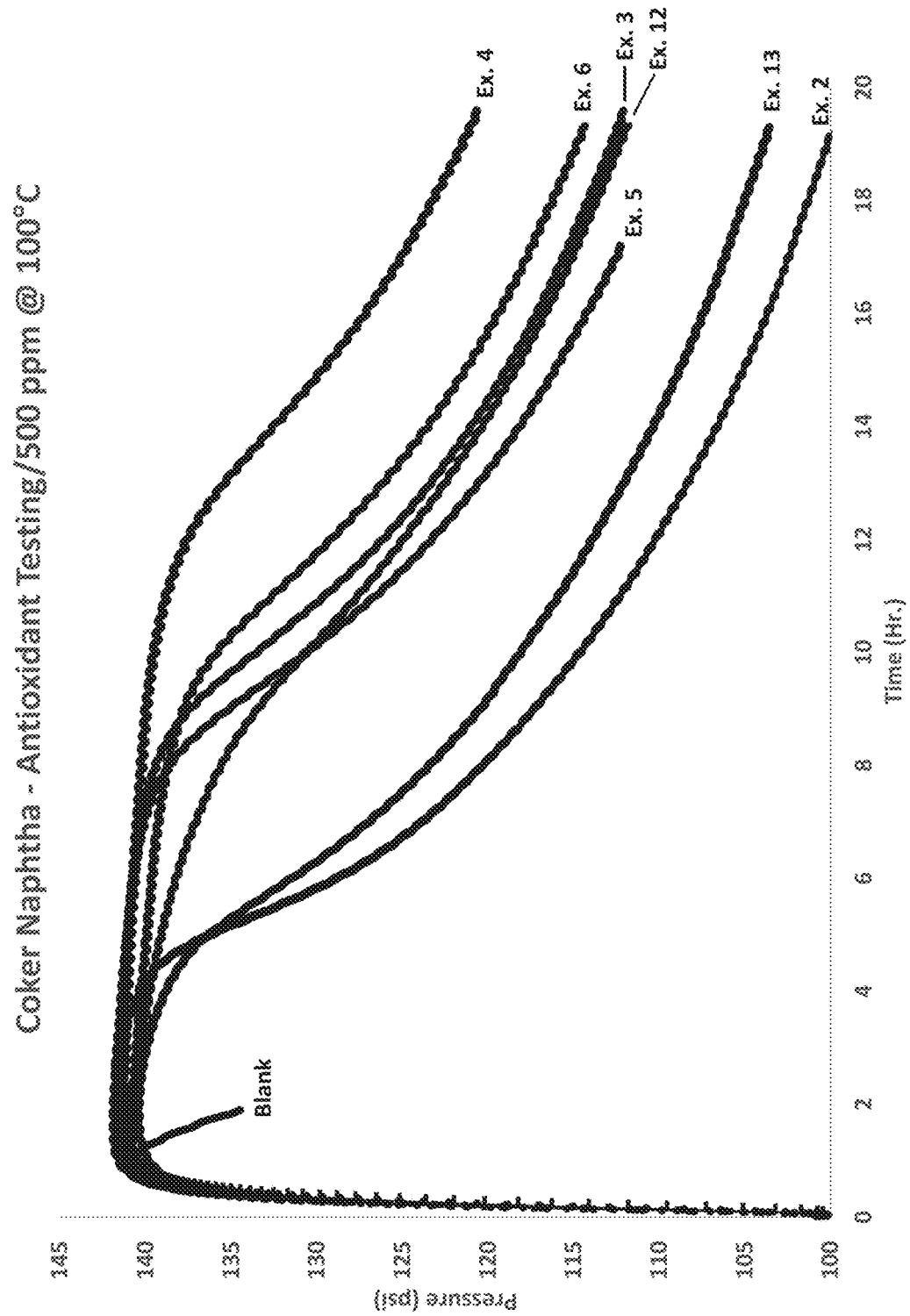
FIG. 4 is a graph of change in pressure over time as determined from antioxidant testing of various oxygenated aromatic amines of the disclosure with coker naphtha.

The effectiveness of compounds of the disclosure to stabilize coker naphtha, solutions of various oxygenated aromatic amines according to Examples 2-13 were prepared in heavy aromatic naphtha and tested according to the ASTM D525 method, as described in Example 14. In this example, the oxygenated aromatic amines antioxidants were used at 500 ppm Results are shown in FIG. 4, and illustrate change in pressure overtime.

What is claimed is:

1. A method for inhibiting oxidation of an organic compound, the method comprising:
(1a) adding a compound of Formula Ia to a composition comprising an organic compound, the compound of Formula Ia being:

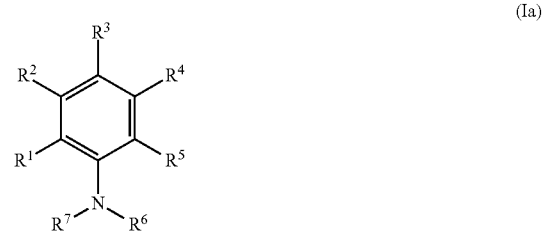

(Ia)

wherein —$R^1$, —$R^2$, —$R^3$, —$R^4$, and —$R^5$ are independently selected from —H, —OH, alkyl, aryl, alkyl aryl, and aryl alkyl, or any two adjacent groups of —$R^1$, —$R^2$, —$R^3$, —$R^4$, and —$R^5$ form one or more ring structures;

wherein both of $R^6$ and $R^7$ are of the formula: —$(CR^{10}_2)_q(CHOH)(CH_2)_zR^{11}$, wherein $R^{10}$ is independently selected from —H and alkyl, q and z are independently 0 (a covalent bond) or an integer in the range of 1-12, and $R^{11}$ is selected from the group consisting of C1-C24 linear, branched, or cyclic alkyl, aryl, alkyl-aryl, and aryl-alkyl; or wherein one or both of $R^6$ and $R^7$ are of the formula: —$(CR^{10}_2)_q(CHOH)(R^{12}O)_zR^{11}$, wherein $R^{10}$ is independently selected from —H and alkyl, q is 0 (a covalent bond) or an integer in the range of 1-12, $R^{11}$ is selected from the group consisting of C1-C24 linear, branched, or cyclic alkyl, aryl, alkyl-aryl, and aryl-alkyl, and $R^{12}$ is independently selected from —$(CH_2)_w$—, wherein w is 1, 2, or 3, and z is an integer in the range of 1-5; and one of $R^6$ and $R^7$ is optionally —H, alkyl, aryl, alkyl-aryl, aryl-alkyl, or a carbon-containing group including one or more hydroxyl group(s) separated from the N atom by one or more carbon atoms; or (1b) adding a compound of Formula Ib to a composition comprising an organic compound, the compound of Formula Ib being:

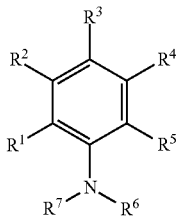

wherein —R$^1$, —R$^2$, —R$^3$, —R$^4$, and —R$^5$ are independently selected from —H, OH, alkyl, aryl, alkyl aryl and aryl alkyl, and —NR$^8$R$^9$, wherein R$^8$ and R$^9$ are independently selected from —H, alkyl, aryl, alkyl aryl and aryl alkyl, and R$^6$/R$^7$ as described herein, or any two adjacent groups of —R$^1$, —R$^2$, —R$^3$, —R$^4$, and —R$^5$ form one or more ring structures;

wherein one or both of R$^6$ and R$^7$ include at least two oxygens, at least one oxygen in the form of an ether group, and at least one oxygen in the form of a hydroxyl group, wherein the one or more hydroxyl group(s) are separated from the N atom by one or more carbon atoms, wherein one or both of R$^6$ and R$^7$ are of the formula —(CR$^{10}_2$)$_q$(CHOH)(R$^{12}$O)$_z$R$^{11}$, wherein R$^{10}$ is independently selected from —H and alkyl, q is 0 (a covalent bond) or an integer in the range of 1-12, R$^{11}$ is selected from the group consisting of C1-C24 linear, branched, or cyclic alkyl, aryl, alkyl-aryl, and aryl-alkyl, and R$^{12}$ is independently selected from —(CH$_2$)$_w$—, wherein w is 1, 2, or 3, and z is an integer in the range of 1-5;

wherein the compound of Formula Ia or Formula Ib inhibits oxidation of the organic compound in the composition, and wherein (I) the organic compound is present in a lubricant composition, (II) the organic compound is present in a fuel composition that is a gasoline or a gasoline blend comprises pyrolysis gasoline, a refined product of pyrolysis gasoline, ethanol, or a combination thereof, or (III) the organic compound is present in (a) a rubber composition, a plastic composition, or an adhesive composition, or (b) a food or beverage composition.

2. The method of claim 1 wherein the organic compound comprises an ethylenically unsaturated group, the organic compound being an olefin or alkene.

3. The method of claim 1 wherein the organic compound is present in (I) or (II).

4. The method of claim 1 wherein the compound of Formula Ia or Formula Ib is present in the composition in an amount in the range of 1 ppm to 5000 ppm.

5. The method of claim 4 wherein the compound of Formula Ia or Formula Ib is present in the composition in an amount in the range of 10 ppm to 2500 ppm, or optionally in an amount in the range of 50 ppm to 1500 ppm.

6. The method of claim 1, wherein at least one of —R$^1$, —R$^2$, —R$^3$, —R$^4$, and —R$^5$ is —OH.

7. The method of claim 1 wherein Formula Ia or Formula Ib, the one or more hydroxyl group(s) are separated from the N atom by two or more carbon atoms.

8. The method of claim 7, wherein the one or more hydroxyl group(s) are separated from the N atom by two carbon atoms.

9. The method of claim 6, wherein —R$^1$, —R$^2$, —R$^3$, —R$^4$, and —R$^5$ that is or are not —OH are —H.

10. The method of claim 1 wherein Formula Ia both of R$^6$ and R$^7$ are of the formula: —(CR$^{10}_2$)$_q$(CHOH)(CH$_2$)$_z$R$^{11}$.

11. The method of claim 10 wherein the compound is selected from the group consisting of: 4-bis[(2-hydroxyethyl)amino]phenol, 4-bis[(2-hydroxypropyl)amino]phenol, 4-bis[(2-hydroxybutyl)amino]phenol, 4-bis[(2-hydroxypentyl)amino]phenol, 4-bis[(2-hydroxyhexyl)amino]phenol, 4-bis[(2-hydroxy-2-phenyl)amino]phenol, 4-bis[(2-hydroxy-2-phenylethyl)amino]phenol, 4-bis[(2-hydroxyheptyl)amino]phenol, 4-bis[(2-hydroxyoctyl)amino]phenol, 4-bis[(2-hydroxynonyl)amino]phenol, 4-bis[(2-hydroxydecyl)amino]phenol, 4-bis[(2-hydroxyundecyl)amino]phenol, 4-bis[(2-hydroxydodecyl)amino]phenol, 4-bis[(2-hydroxytridecyl)amino]phenol, 4-bis[(2-hydroxytetradecyl)amino]phenol, 4-bis[(2-hydroxypentadecyl)amino]phenol, 4-bis[(2-hydroxyhexadecyl)amino]phenol, 4-bis[(2-hydroxyheptadecyl)amino]phenol, 4-bis[(2-hydroxyoctadecyl)amino]phenol, 4-bis[(2-hydroxyeleyl)amino]phenol, 4-bis[(2-hydroxynonadecyl)amino]phenol, 4-bis[(2-hydroxyeicosyl)amino]phenol, 4-bis[(2-hydroxyheneicosyl)amino]phenol, 4-bis[(2-hydroxydocosyl)amino]phenol, and 4-bis[(2-hydroxytricosyl)amino]phenol.

12. The method of claim 1, wherein Formula Ia, both of R$^6$ and R$^7$ are of the formula: —(CR$^{10}_2$)$_q$(CHOH)(R$^{12}$O)$_z$R$^{11}$.

13. The method of claim 12, wherein q is 0 (a covalent bond), 1, or 2.

14. The method of claim 1, wherein Formula Ia R$^{10}$ is —H, q is 1; s is 1; w is 1 or 2, and R$^{11}$ is C1-C18 linear, branched, or cyclic alkyl, aryl, alkyl-aryl, and aryl-alkyl.

15. The method of claim 14, wherein the compound is selected from the group consisting of 4-bis[(3-methoxy-2-hydroxy-propyl)amino]phenol, 4-bis[(3-ethoxy-2-hydroxy-propyl)amino]phenol, 4-bis[(3-propoxy-2-hydroxy-propyl)amino]phenol, 4-bis[(3-butoxy-2-hydroxy-propyl)amino]phenol, 4-bis[(3-pentyloxy-2-hydroxy-propyl)amino]phenol, 4-bis[(3-hexyloxy-2-hydroxy propyl)amino]phenol, 4-bis[(3-heptyloxy-2-hydroxy-propyl)amino]phenol, 4-bis[(3-octyloxy-2-hydroxy-propyl)amino]phenol, 4-bis[(3-nonyloxy-2-hydroxy-propyl)amino]phenol, 4-bis[(3-decyloxy-2-hydroxy-propyl)amino]phenol, 4-bis[(3-undecyloxy-2-hydroxy-propyl)amino]phenol, 4-bis[(3-dodecyloxy-2-hydroxy-propyl)amino]phenol, 4-bis[(3-tridecyloxy-2-hydroxy-propyl)amino]phenol, 4-bis[(3-tetradecyloxy-2-hydroxy-propyl)amino]phenol, 4-bis[(3-pentadecyloxy-2-hydroxy-propyl)amino]phenol, 4-bis[(3-hexadecyloxy-2-hydroxy-propyl)amino]phenol, 4-bis[(3-heptadecyloxy-2-hydroxy-propyl)amino]phenol, 4-bis[(3-octadecyloxy-2-hydroxy-propyl)amino]phenol, 4-bis[(3-eleyloxy-2-hydroxy-propyl)amino]phenol, 4-bis[(3-nonadecyloxy-2-hydroxy-propyl)amino]phenol, 4-bis[(3-eicosyloxy-2-hydroxy-propyl)amino]phenol, 4-bis[(3-heneicosyloxy-2-hydroxy-propyl)amino]phenol, 4-bis[(3-docosyloxy-2-hydroxy-propyl)amino]phenol, and 4-bis[(3-tricosyloxy-2-hydroxy propyl)amino]phenol.

16. The method of claim 1, wherein Formula Ib at least one of —R$^1$, —R$^2$, —R$^3$, —R$^4$, and —R$^5$ is NR$^8$R$^9$.

17. The method of claim 16, wherein the compound is selected from the group consisting of 1,4-bis[3-methoxy-2-hydroxy-propylamino]benzene, 1,4-bis[3-ethoxy-2-hydroxy-ethylamino]benzene, 1,4-bis[3-propoxy-2-hydroxy-propylamino]benzene, 4-bis[3-butoxy-2-hydroxy-propylamino]benzene, 1,4-bis[3-pentyloxy-2-hydroxy-propylamino]benzene, 1,4-bis[3-hexyloxy-2-hydroxy-propylamino]benzene, 1,4-bis[3-heptyloxy-2-hydroxy-propylamino]benzene, 1,4-bis[3-octyloxy-2-hydroxy-propylamino]benzene, 1,4-bis[3-nonyloxy-2-hydroxypropylamino]benzene, 1,4-bis[3-decyloxy-2-hydroxy-propylamino]benzene, 1,4-bis[3-undecyloxy-2-hydroxy-propylamino]benzene, 1,4-bis[3-dodecyloxy-2-hydroxy-propylamino]benzene, 1,4-bis[3-tridecyloxy-2-hydroxy-propylamino]benzene, 1,4-bis[3-tetradecyloxy-2-hydroxy-propylamino]benzene, 1,4-bis[3-pentadecyloxy-2-hydroxy-propylamino]benzene, 1,4-bis[3-hexadecyloxy-2-hydroxy-propylamino]benzene, 1,4-bis[(3-heptadecyloxy-2-hydroxy-propylamino]benzene, 1,4-bis[3-octadecyloxy-2-hydroxy-propylamino]benzene, 1,4-bis[3-eleyloxy-2-hydroxy-propylamino]benzene, 1,4-bis[3-nonadecyloxy-2-hydroxy-propylamino]benzene, 1,4-bis[3-eicosyloxy-2-hydroxy-propylamino]benzene, 1,4-bis[3-heneicosyloxy-2-hydroxy-propylamino]benzene, 1,4-bis[3-docosyloxy-2-hydroxy-propylamino]benzene, and 1,4-bis[3-tricosyloxy-2-hydroxy-propylamino]benzene.

18. The method of claim 1 wherein the compound of Formula Ib is prepared by reacting an aryl-group containing reactant from the group consisting of 4-aminophenol, 1,4-diaminobenzene (p-phenylenediamine), and dimethyl-4-phenylenediamine with a carbon and oxygen-containing reactant that comprises an oxirane- and oxitane-containing reactant of Formula II:

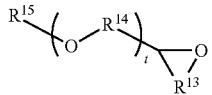

wherein $R^{13}$ is —(CH$_2$)— or —(CH$_2$CH$_2$)—, wherein $R^{14}$ is —(CH$_2$)$_w$—, wherein w is an integer in the range of 1-3, t is an integer in the range of 1-100, and wherein $R^{15}$ is $R^{10}$, as described herein.

19. The method of claim 1 wherein Formula Ia q and z are independently 0, 1, or 2; and $R^{11}$ is C1-C18 linear, branched, or cyclic alkyl, aryl, alkyl-aryl, and aryl-alkyl.

20. The method of claim 1, wherein Formula Ia both of $R^6$ and $R^7$ are the (1) carbon-containing group including one or more hydroxyl group(s) separated from the N atom by one or more carbon atoms, or wherein Formula Ib both of $R^6$ and $R^7$ are of the formula —(CR$^{10}_2$)$_q$(CHOH)(R$^{12}$O)$_z$R$^{11}$.

21. A method for inhibiting oxidation of an organic compound, the method comprising:
(1a) adding a compound of Formula Ia to a composition comprising an organic compound, the compound of Formula Ia being:

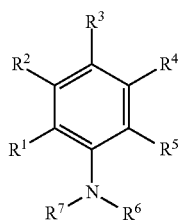

(Ia)

wherein —R$^1$, —R$^2$, —R$^3$, —R$^4$, and —R$^5$ are independently selected from —H, —OH, alkyl, aryl, alkyl aryl, and aryl alkyl, wherein at least one of —R$^1$, —R$^2$, —R$^3$, —R$^4$, and —R$^5$ is —OH, or any two adjacent groups of —R$^1$, —R$^2$, —R$^3$, —R$^4$, and —R$^5$ form one or more ring structures;

wherein both of R$^6$ and R$^7$ are carbon-containing groups including one or more hydroxyl group(s) separated from the N atom by one or more carbon atoms; or
(1b) adding a compound of Formula Ib to a composition comprising an organic compound, the compound of Formula Ib being:

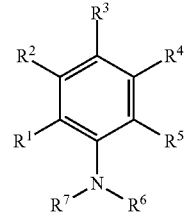

(Ib)

wherein —R$^1$, —R$^2$, —R$^3$, —R$^4$, and —R$^5$ are independently selected from —H, —OH, alkyl, aryl, alkyl aryl and aryl alkyl, and —NR$^8$R$^9$, wherein R$^8$ and R$^9$ are independently selected from —H, alkyl, aryl, alkyl aryl and aryl alkyl, and R$^6$/R$^7$ as described herein, or any two adjacent groups of —R$^1$, R$^2$, —R$^3$, —R$^4$, and —R$^5$ form one or more ring structures, and wherein at least one of —R$^1$, —R$^2$, —R$^3$, —R$^4$, and —R$^5$ is —OH;

wherein both of R$^6$ and R$^7$ include at least two oxygens, at least one oxygen in the form of an ether group, and at least one oxygen in the form of a hydroxyl group, wherein the one or more hydroxyl group(s) are separated from the N atom by one or more carbon atoms;

wherein the compound of Formula Ia or Formula Ib inhibits oxidation of the organic compound in the composition.

22. A method for inhibiting oxidation of an organic compound, the method comprising:
(1a) adding a compound of Formula Ia to a composition comprising an organic compound, the compound of Formula Ia being:

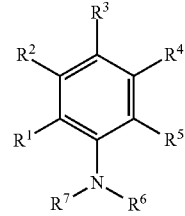

(Ia)

wherein —R$^1$, —R$^2$, —R$^3$, —R$^4$, and —R$^5$ are independently selected from —H, —OH, alkyl, aryl, alkyl aryl, and aryl alkyl, or any two adjacent groups of —R$^1$, —R$^2$, —R$^3$, —R$^4$, and R$^5$ form one or more ring structures;

wherein one or both of R$^6$ and R$^7$ are:
(I) of the formula: —(CR$^{10}_2$)$_q$(CHOH)(CH$_2$)$_z$R$^{11}$, R$^{10}$ is independently selected from —H and alkyl, wherein q and z are independently 0 (a covalent bond), or an integer in the range of 1-12, and R$^{11}$ is selected from the group consisting of C1-C24 linear, branched, or cyclic alkyl, aryl, alkyl-aryl, and aryl-alkyl,
(II) of the formula: —(CR$^{10}_2$)$_q$(CHOH)(R$^{12}$O)$_z$R$^{11}$, R$^{10}$ is independently selected from —H and alkyl, q is 0 (a covalent bond) or an integer in the range of 1-12, $R^{11}$ is selected from the group consisting of C1-C24 linear, branched, or cyclic alkyl, aryl, alkyl-aryl, and aryl-alkyl, and $R^{12}$ is independently selected from —$(CH_2)_w$—, wherein w is 1, 2, or 3, and z is an integer in the range of 1-5; or (1b) adding a compound of Formula Ib to a composition comprising an organic compound, the compound of Formula Ib being:

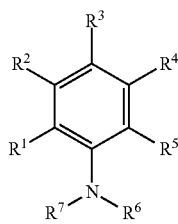

(Ib)

wherein —$R^1$, —$R^3$, —$R^3$, —$R^4$, and —$R^5$ are independently selected from —H, —OH, alkyl, aryl, alkyl aryl and aryl alkyl, and —$NR^8R^9$, wherein $R^8$ and $R^9$ are independently selected from —H, alkyl, aryl, alkyl aryl and aryl alkyl, and $R^6/R^7$ as described herein, or any two adjacent groups of —$R^1$, —$R^2$, —$R^3$, —$R^4$, and —$R^5$ form one or more ring structures;

wherein one or both of $R^6$ and $R^7$ are of the formula: —$(CR^{10}_2)_q(CHOH)(R^{12}O)_zR^{11}$, $R^{10}$ is independently selected from —H and alkyl, q is 0 (a covalent bond) or an integer in the range of 1-12, $R^{11}$ is selected from the group consisting of C1-C24 linear, branched, or cyclic alkyl, aryl, alkyl-aryl, and aryl-alkyl, and $R^{12}$ is independently selected from —$(CH_2)_w$—, wherein w is 1, 2, or 3, and z is an integer in the range of 1-5;

wherein the compound of Formula Ia or Formula Ib inhibits oxidation of the organic compound in the composition.

* * * * *